(12) United States Patent
Raney et al.

(10) Patent No.: US 7,279,618 B2
(45) Date of Patent: Oct. 9, 2007

(54) **SEEDS, OILS AND SEED MEALS PRODUCED FROM *SINAPIS ALBA***

(75) Inventors: John Philip Raney, Clavet (SK); Gerhard F. Rakow, Saskatoon (CA)

(73) Assignee: Her Majesty the Queen in Right of Canada, as Represented by Agriculture and Agri-Food Canada, Saskatchewan (CA)

( * ) Notice: Subject to any disclaimer, the term of this patent is extended or adjusted under 35 U.S.C. 154(b) by 577 days.

(21) Appl. No.: 10/204,142

(22) PCT Filed: Feb. 16, 2001

(86) PCT No.: PCT/CA01/00183

§ 371 (c)(1),
(2), (4) Date: Jan. 6, 2003

(87) PCT Pub. No.: WO01/60145

PCT Pub. Date: Aug. 23, 2001

(65) Prior Publication Data

US 2003/0182677 A1    Sep. 25, 2003

Related U.S. Application Data

(60) Provisional application No. 60/183,387, filed on Feb. 18, 2000.

(51) Int. Cl.
*A01H 5/10*      (2006.01)
(52) U.S. Cl. ................... 800/306; 800/295; 800/298
(58) Field of Classification Search ............... 800/295, 800/298, 306
See application file for complete search history.

(56) References Cited

OTHER PUBLICATIONS

ManCan Ingredients, Inc., Co-operative Mustard Test, 1995, http://www.mancan.mb.ca/coop 1995.html.*
Raney et al. 1995. Proceedings of the 9th International Rapeseed Congress, vol. 2, pp. 416-418.*
Tang. 1996. University of Idaho Thesis Abstract.*
Bell, et al., "Comparisons of amino acid and protein levels in oil-extracted seeds of *Brassica* and *Sinapis* species, with observations on environmental effects," *Canadian Journal of Animal Science* pp. 169-174 (1999).
Brandt, S.A., "Depths, rates and dates of seeding and yield of yellow mustard (*Sinapis alba* L.) In west-central Saskatchewan," *Canadian Journal of Plant Science* 72:351-359 (1992).
Brown, et al., "Developing Canola-Quality Cultivars of Yellow Mustard (*Sinapis alba* L.)," *New Horizons for an Old Crop, Proceedings of the 10th International Rapeseed Congress*, Canberra, Australia (1999) 17 pages.

Downey et al., "Mustard," *Harvest of Gold: The History of Field Crop Breeding in Canada*, pp. 213-219 (1995).
Drost, et al., "Inheritance of Erucic Acid Content in Yellow Mustard (*Sinapis alba* L.)," *New Horizons for an Old Crop, Proceedings of the 10th International Rapeseed Congress*, Canberra, Australia (1999) 4 pages.
Drost, et al., "Inheritance of Glucosinolate Content in Yellow Mustard (*Sinapis alba* L.)," *New Horizons for an Old Crop, Proceedings of the 10th International Rapeseed Congress*, Canberra, Australia (1999) 4 pages.
Eskin, et al., "Stability of Low Linolenic Acid Canola Oil to Frying Temperatures," *JAOCS* 66:1081-1084 (1989).
Katepa-Mupondwa, et al., "Developing Oilseed Yellow Mustard (*Sinapis alba* L.) In Western Canada," *New Horizons for an Old Crop, Proceedings of the 10th International Rapeseed Congress*, Canberra, Australia (1999) 3 pages.
Katepa-Mupondwa, et al, "Meal Quality Characteristics Yellow Mustard (*Sinapis alba* L.)," *New Horizons for an Old Crop, Proceedings of the 10th International Rapeseed Congress*, Canberra, Australia (1999) 3 pages.
Krzymanski, et al., "Development of Low Glucosinolate White Mustard (*Sinapis alba* Syn. *Brassica hirta*)," *GCIRC 1991 Congress*, pp. 1545-1548 (1991).
Landerouin, et al., "Optimization of Silylation Reactions of Desulphoglucosinolates Before Gas Chromatography," *World Crops*, pp. 26-37.
Olsson, Gosta, "Continuous selection for seed number per pod and oil content in white mustard," *Hereditas* 77:197-204 (1974).
Prevot, et al., "A New Variety of Low-Linolenic Rapeseed Oil; Characteristics and Room-Odor Tests," *JAOCS* 67:161-164 (1990).
Raney, et al., "Development of High Erucic, Low Glucosinolate *Sinapis alba*," *D19; Breeding: Oil Quality* pp. 452-455 (1995).
Raney, et al., "Development of low Erucic, Low Glucosinolate *Sinapis alba*," *D12: Breeding: Oil Quality*, pp. 416-418 (1995).
Raney, et al., "Selection for High Oleic Acid in 'zero' Erucic Acid *Sinapis alba*," *New Horizons for an Old Crop, Proceedings of the 10th International Rapeseed Congress*, Canberra, Australia (1999) 4 pages.
Scarth, et al., "Apollo low linolenic summer rape," *Canadian Journal of Plant Science* 75:203-204 (1994).
Ecker, R., et al., "Genetic control of fatty acid composition in seed oil of *Sinapis alba* L.," *Euphytica*, 69:45-49 (1993).

* cited by examiner

*Primary Examiner*—David H. Kruse
*Assistant Examiner*—Keith O. Robinson
(74) *Attorney, Agent, or Firm*—Quarles & Brady LLP

(57) ABSTRACT

The present invention provides oil seeds obtained from *Sinapis alba* that have a high level of oleic acid (from about 72 to about 84% by weight), a low level of erucic acid (from 0.0 to about 0.2% by weight), low levels of p-hydroxybenzyl glucosinolate and benzyl glucosinolate (each less than or equal to about 0.1 mole per g seed), or a combination thereof. Also provided are plants that produce such oil seeds. Also disclosed are oil seeds having high levels of erucic acid (greater than about 55% by weight) and low levels of p-hydroxybenzyl glucosinolate and benzyl glucosinolate (each less than about 0.1 mole per g seed), and plants that produce such oil seed.

4 Claims, 7 Drawing Sheets

FIGURE 2 -

SEEDS, OILS AND SEED MEALS PRODUCED FROM *SINAPIS ALBA*

CROSS-REFERENCE TO RELATED APPLICATIONS

This application claims priority from PCT Application No. PCT/CA01/00183 filed Feb. 16, 2001 which claimed priority from US Provisional Application No. 60/183,387 filed Feb. 18, 2000. These applications are incorporated by reference herein in their entirety.

The present invention relates to seeds, oils and seed meal obtained from *Sinapis alba* L. plants. Furthermore, this invention pertains to *S. alba* plants that produce these seeds, oils and meals. More particularly, the present invention relates to oil seeds comprising a high oleic acid, low glucosinolate, and either a high or low erucic acid content or oil seeds with a low glucosinolate, high erucic acid content. The products obtained from these oil seeds are suitable for human and animal consumption, and industrial applications.

BACKGROUND OF THE INVENTION

*Sinapis alba* has successfully been grown as a condiment crop on the western Canadian prairie for many years. It has many agronomic advantages for dryland production over *Brassica napus, B. rapa* and *B. juncea*. The most important aspect is its excellent heat and drought tolerance. Seed pods are highly shatter-resistant allowing direct combining of the crop. *Sinapis alba* is highly resistant to blackleg disease, a serious disease of *B. napus* canola. It also has useful levels of flea beetle resistance, a serious pest of *B. napus* and *B. rapa* and can survive moderate flea beetle attack without insecticidal protection, thereby reducing or eliminating the need for insecticides against flea beetle. *Sinapis alba* is large seeded (5-6 g per 1000 seeds) compared to the *Brassica* oilseeds (2.5-3.5 g per 1000 seeds). This larger seed size allows *S. alba* to be planted into moisture up to a 50 mm depth, whereas shallow seeding is required for *Brassica* type crops. *Sinapis alba* seed is of a bright yellow colour, a much-desired trait in the typically black-seeded *B. napus* species.

Despite the many agronomic advantages of *S. alba*, it is not grown as an oilseed in Canada, because the seed is relatively high in erucic acid (C22:1) and glucosinolate content and has a low oil content (about 28%). *Sinapis alba* seed oil of condiment mustard varieties such as AC Pennant contains about 35% erucic acid (Downey and Rakow 1995). Although erucic acid toxicity has not been demonstrated in humans, this fatty acid has been associated with poor performance and abnormal lipid metabolism in heart and skeletal muscle tissue in laboratory animals and pigs.

Both, a line with 3-4% by weight erucic acid (e.g. BHL3-926), and a high erucic acid variety having an erucic acid content over 55% (for example 'Sabre') *S. alba* strains have been developed at the Agriculture and Agri-Food Canada, Saskatoon Research Centre. *Sinapis alba* lines having very low p-hydroxybenzyl glucosinolate are known, e.g. (Brown et al. 1999, Krzymanski et al. 1991, and Raney et al. 1995a & 1995b). However, these lines have elevated levels of 2-hydroxy-3-butenyl glucosinolate and benzyl glucosinolate thereby limiting the utility of oil-free meal prepared from these oil seeds following oil extraction. Glucosinolates reduce palatability and feed intake in non-ruminant animals, and inhibit iodine uptake by the thyroid gland, causing goitre and other growth and reproductive anomalies. Of particular concern is benzyl glucosinolate which is not found in canola (*B. napus* and *B. rapa*) or mustard (*B. juncea* and *S. alba*) and therefore may have other possible deleterious properties. In order to ensure the success of *S. alba* as an agricultural crop, the oil must exhibit desired properties for either human or industrial use, and the seed meal should also have a high value use, for example, in livestock or fish feed formulations or in human processed food products.

The oil free meal in *S. alba* possesses a relatively high protein content (45-48%) and the amino acid composition of the meal is fairly well balanced. Compared to soybean and canola, *S. alba* protein contains less of the amino acid lysine, but more of the sulphur amino acids methionine and cystine. The high concentration of glucosinolates in *S. alba* meal has discouraged its use in animal feed formulations. *Sinapis alba* has found use in human food applications as a condiment and, because of its relatively high protein and mucilage content, in prepared foods as an animal protein extender, binding agent or emulsifying agent. Such uses require only limited acres of *S. alba* to satisfy demand.

Therefore, for *S. alba* to become a high quality edible oilseed crop, low erucic acid strains, with a high oil content, preferably with a high oleic acid and low linolenic acid content, need to be developed. To ensure that the oil-free meal may be used as an animal feed, then the total glucosinolate level (responsible for the bitter taste of *S. alba* seed) within such lines must be as low as possible. Furthermore, to produce quality industrial oils, *S. alba* oil seed comprising high levels of erucic acid, with low glucosinolate levels are also required, ensuring market acceptability for both the extracted oil, and the oil-free meal.

*Brassica napus* L. (Argentine canola) is an important edible oil crop. The area planted to canola in western Canada was 4,052,400 hectares annually, average for the 10-year period 1989 to 1998, 90% of which is *B. napus*. The area of production for *B. napus* is limited because canola has limited heat and drought tolerance. Therefore, alternate sources of plant oil produced from a hardier plant, for example from *S. alba*, is desired. However, to be commercially acceptable, the oil and meal produced by *S. alba* must exhibit the minimum standard of characteristics found within that prepared from *B. napus*.

*Sinapis alba* and *Brassica* species are very different in the types of glucosinolates present in their seeds. The major glucosinolate in *Sinapis alba* seed is p-hydroxybenzyl glucosinolate (140-150 μmoles per g of seed), which gives *S. alba* seed its bitter taste. It is not found in *Brassica* species seed such as *B. napus, B. rapa, B. juncea*, or *B. carinata*. *Brassica* species seed contain high concentrations of allyl, 3-butenyl, 4-pentenyl, 2-hydroxy-3-butenyl and 2-hydroxy-4-pentenyl glucosinolates totalling 100 μmoles per gram of seed or more. In canola strains of these species, except for *B. carinata* which so far no low glucosinolate lines have been developed, the total glucosinolate content is much reduced (less than 18 μmoles per g seed).

Low glucosinolate *S. alba* lines have been developed comprising total glucosinolate contents ranging from about 15 μmoles per g seed to about 40 μmoles per g seed (Krzymanski et al. 1991). In addition to low levels of p-hydroxybenzyl glucosinolate, these varieties also contain 5-10 μmoles per g of seed of 2-hydroxy-3-butenyl glucosinolate and benzyl glucosinolate. These low glucosinolate *S. alba* lines have normal erucic acid contents (approx. 28% by weight) in their seed oil.

The erucic acid content in *S. alba* is controlled by a single gene exhibiting partial dominance of high over zero erucic acid contents (Drost et al. 1999a; Brown et al., 1999). Similarly, the inheritance of p-hydroxybenzyl glucosinolate is also controlled by a single gene with high p-hydroxybenzyl glucosinolate content dominant over low p-hydroxybenzyl glucosinolate content (Drost et al. 1999b; Brown et al., 1999). Moderately low erucic acid (0.5 to 2.7%), and low p-hydroxybenzyl glucosinolate (0.0 to 0.1 μmoles per g seed) S. alba from crosses between moderately low erucic acid and low p-hydroxybenzyl glucosinolate S. alba lines have been developed (Raney et al. 1995a; Brown et al., 1999) towards the objective of obtaining an S. alba that can produce a canola-quality type low in erucic acid oil and low in glucosinolate canola-quality high protein meal. The amount of oleic acid within oil obtained from these oilseeds ranges from 54 to 72%. Any increase in the levels of oleic acid in seed oil of S. alba is desirable for human consumption. It is also desired that the levels of linolenic acid be low as this component is known to reduce the stability of the oil (White and Miller 1998; Scarth et al., 1994; Eskin et al. 1989; Przybyski et al. 1993; Prevot et al., 1990). Furthermore, reduction in the glucosinolate content within oil seeds ensures high value use of the seed meal obtained following oil extraction.

Despite all these efforts, the need remains for a S. alba line which combines superior edible oil quality (high oleic acid, low linolenic acid) with the lowest possible glucosinolate content. Similarly, for industrial applications, there is a need for a S. alba line from which oil seed comprising high erucic acid, and low glucosinolate content may be obtained. Furthermore to be acceptable as an oilseed crop, the line must have a high oil content, it must be genetically stable for these traits, and it must retain the positive agronomic attributes of S. alba, such as adaptation to dryland agriculture and resistance to diseases and pests, in combination with acceptable seed yields.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to an oil seed from *Sinapis alba* comprising from about 72 to about 84%, by weight, oleic acid. Also included in this invention is a plant that produces the oil seed as defined above, and an oil prepared from the oil seed.

The present invention also relates to an oil seed from *Sinapis alba* comprising from about 0.0 to about 0.2%, by weight, erucic acid. Also included in this invention is a plant that produces an oil seed comprising from about 0.0 to about 0.2% erucic acid, and an oil prepared from the oil seed.

Furthermore, the present invention provides for an oil seed from *Sinapis alba* comprising less than about 0.1 μmole per g seed of p-hydroxybenzyl glucosinolate, and less than about 0.1 μmole per g seed of benzyl glucosinolate. Also included in this invention are plants that produce the oil seed comprising less than about 0.1 μmole per g seed of p-hydroxybenzyl glucosinolate, and less than about 0.1 μmole per g seed of benzyl glucosinolate, and oil free meal prepared from the oil seed.

The present invention relates to an oil seed obtained from *Sinapis alba* comprising:
 oleic acid of about 72 to about 84% (by weight);
 linoleic acid of less than about 11%;
 linolenic acid of about 6 to about 10%; and
 erucic acid of about 0.0 to about 1.0%.

This invention also pertains to the oil seed defined above, further comprising p-hydroxybenzyl glucosinolate of less than 0.1 μmoles per g of seed and benzyl glucosinolate of less than 0.1 μmoles per g of seed. Also included in the present invention is a plant that produces the oil seed. This invention also embraces the oil extracted from the oil seed as defined above, and oil free meal prepared from the oil seed.

The present invention also relates to an oil seed obtained from *Sinapis alba* comprising:
 oleic acid of about 55 to about 84% (by weight);
 linoleic acid of less than about 11%;
 linolenic acid of about 6 to about 10%; and
 erucic acid of about 0.0 to about 0.2%.

This invention also pertains to the oil seed defined above, further comprising p-hydroxybenzyl glucosinolate of less than 0.1 μmoles per g of seed and benzyl glucosinolate of less than 0.1 μmoles per g of seed. Also included in the present invention is a plant that produces the oil seed. This invention also embraces the oil extracted from the oil seed as defined above, and an oil free meal prepared from the oil seed.

The present invention embraces a method for producing an S. alba plant, or oil seed from an S. alba plant, comprising:
 i) selecting individual S. alba seed having a low erucic acid content and propagating plants from selected seed by open pollination or self pollination;
 ii) selecting individual $F_2$ seeds with a low erucic acid, high oleic acid, and low linolenic acid content, crossing, and propagating plants from selected $F_2$ seed;
 iii) repeating step ii) from 1 to about n times to obtain selected $F_n$ seed;
 iv) growing a plant from the selected $F_n$ seed to produce an oil seed comprising oleic acid of about 72 to about 84% (by weight), linoleic acid of less than about 11%, linolenic acid of about 6 to about 10%, and erucic acid of about 0.0 to about 1.0%.

The present invention also includes a method for producing an S. alba plant, or an oil seed from this plant, comprising:
 i) selecting a first individual seed having a low erucic acid content;
 ii) selecting a second individual seed having a low p-hydroxybenzyl glucosinolate content;
 iii) crossing said first and said second seed to produce $F_2$ seed, and selecting individual $F_2$ seeds with a low erucic acid, high oleic acid, low linolenic acid, and low p-hydroxybenzyl glucosinolate content, and propagating plants from selected $F_2$ seed;
 iii) repeating step iii) form from about 1 to n times to obtain selected $F_n$ seed;
 iv) growing a plant from the selected $F_n$ seed to produce an oil seed comprising oleic acid of about 72 to about 84% (by weight), linoleic acid of less than about 11%, linolenic acid of about 6 to about 10%, and erucic acid of about 0.0 to about 1.0%, and less than about 0.1 μmole per g seed p-hydroxybenzyl glucosinolate.

The present invention also includes the above method, wherein following step iv), the plant is crossed with a high oleic acid plant to produce progeny with a high oleic acid content. Furthermore, this invention also includes a method where, during step iii) of the above method, plants containing low levels of benzyl glucosinolate are also selected, so that selected $F_n$ seed are obtained comprising oleic acid of about 72 to about 84% (by weight), linoleic acid of less than about 11% (by weight), linolenic acid of about 6 to about 10% (by weight), and erucic acid of about 0.0 to about 1.0% (by weight), less than about 0.1 µmole per g seed of p-hydroxybenzyl glucosinolate, and less than about 0.1 µmole per g seed of benzyl glucosinolate.

The present invention therefore relates to the production of *Sinapis alba* oilseed capable of yielding an edible vegetable oil having a distribution of fatty acids accepted as a canola equivalent or superior vegetable oil, following simple crushing and extraction. This invention also pertains to *S. alba* plants that produce such oil seed, and to oil free meal obtained following extraction of the oil.

The present invention provides for oil seed produced from *S. alba* plants that have high oleic acid levels. Any increase in the levels of oleic acid in seed oil of *S. alba* is desirable for the production of vegetable oils for human consumption. Also provided in the present invention are oil seeds having low linolenic acid. Low linolenic acid oils exhibit better stability than oils having higher levels, such as those found in oils typically derived from *S. alba*. This invention also provides for oil seed having a low level of erucic acid. Erucic acid has been associated with poor performance and abnormal lipid metabolism in animals. Furthermore, the present invention provides for oil seed having low levels of p-hydroxybenzyl glucosinolate and benzyl glucosinolate, thereby making the protein meal obtained following oil extraction useful within feeds.

The present invention relates to an oil seed obtained from *Sinapis alba*, the oil of which comprising erucic acid of about 45 to about 65% by weight of total fatty acids. This oil seed further comprising p-hydroxybenzyl glucosinolate of less than 0.1 µmoles per g of seed and benzyl glucosinolate of less than 0.1 µmoles per g of seed. Also included in the present invention is a plant that produces the oil seed. This invention also embraces the oil extracted from the oil seed as defined above, and oil free meal prepared from the oil seed.

The present invention also includes a method for producing an *S. alba* plant or an oil seed from an *S. alba* plant, comprising:

i) selecting a first individual *S. alba* seed having a high erucic acid content, and producing a first plant therefrom;

ii) selecting a second individual *S. alba* seed having a low p-hydroxybenzyl glucosinolate content and producing a second plant therefrom;

iii) crossing the first plant and the second plant to produce $F_1$ seed, followed by $F_2$ seed, and selecting individual $F_2$ seed comprising a high erucic acid content and producing a high erucic acid plant therefrom;

iv) selecting high erucic acid plants comprising low p-hydroxybenzyl glucosinolate and low benzyl glucosinolate; and v) repeating steps iii) and iv) from 1 to n times to obtain selected $F_n$ seed comprising erucic acid of about 45 to about 65% (by weight of total fatty acids) and less than about 0.1 µmoles per g seed of p-hydroxybenzyl glucosinolate and benzyl glucosinolate.

The present invention provides for oil seed produced from *S. alba* plants that have high erucic acid levels. High erucic acid content oils have use in industrial applications as sources of raw material for the production of lubricants, plastics, etc.

The present invention also pertains to:

a plant, or a seed, produced from seed characterized as comprising low erucic acid, high oleic acid, low linoleic acid, and low linolenic acid (TO 96-1704,), and by deposit number ATCC No. PTA-2889;

a plant, or a seed, produced from seed characterized as comprising normal erucic acid, low p-hydroxybenzyl glucosinolate (TO 93-0860), and by deposit number ATCC No. PTA-2895;

a plant, or a seed, produced from seed characterized as comprising low erucic acid, high oleic acid, zero p-hydroxybenzyl glucosinolate (TO 00-5647), and by deposit number ATCC No. PTA-2890;

a plant, or a seed, produced from seed characterized as comprising low erucic acid, low p-hydroxybenzyl glucosinolate, low benzyl glucosinolate line (TO 00-5648), and by deposit number ATCC No. PTA-2891;

a plant, or a seed, produced from seed characterized as comprising high erucic acid, low p-hydroxybenzyl glucosinolate line (TO 00-5650), and by deposit number ATCC No. PTA-2893;

a plant, or a seed, produced from seed characterized as comprising high erucic acid, low p-hydroxybenzyl glucosinolate, low benzyl glucosinolate (TO 00-5649), and by deposit number ATCC No. PTA-2892; and a plant, or a seed, produced from seed characterized as comprising moderately low erucic acid, low p-hydroxybenzyl glucosinolate, and benzyl glucosinolate line, and identified as WD 96-1-3.

The present invention therefore, relates to seeds, oils and seed meal obtained from *Sinapis alba* L. plants, and to *S. alba* plants that produce these seeds, oils and meals. More particularly, the present invention relates to oil seeds comprising a high oleic acid, low glucosinolate, and either a high or low erucic acid content or oil seeds with a low glucosinolate, high erucic acid content. The products obtained from these oil seeds are suitable for human and animal consumption, and industrial applications. Such products have a value equal to or superior to similar products obtained from canola seed for such applications. The invention also relates to processes of forming such plants, and the resulting edible or industrial oils and high protein animal feeds.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein.

DESCRIPTION OF PREFERRED EMBODIMENT

Figure 1:
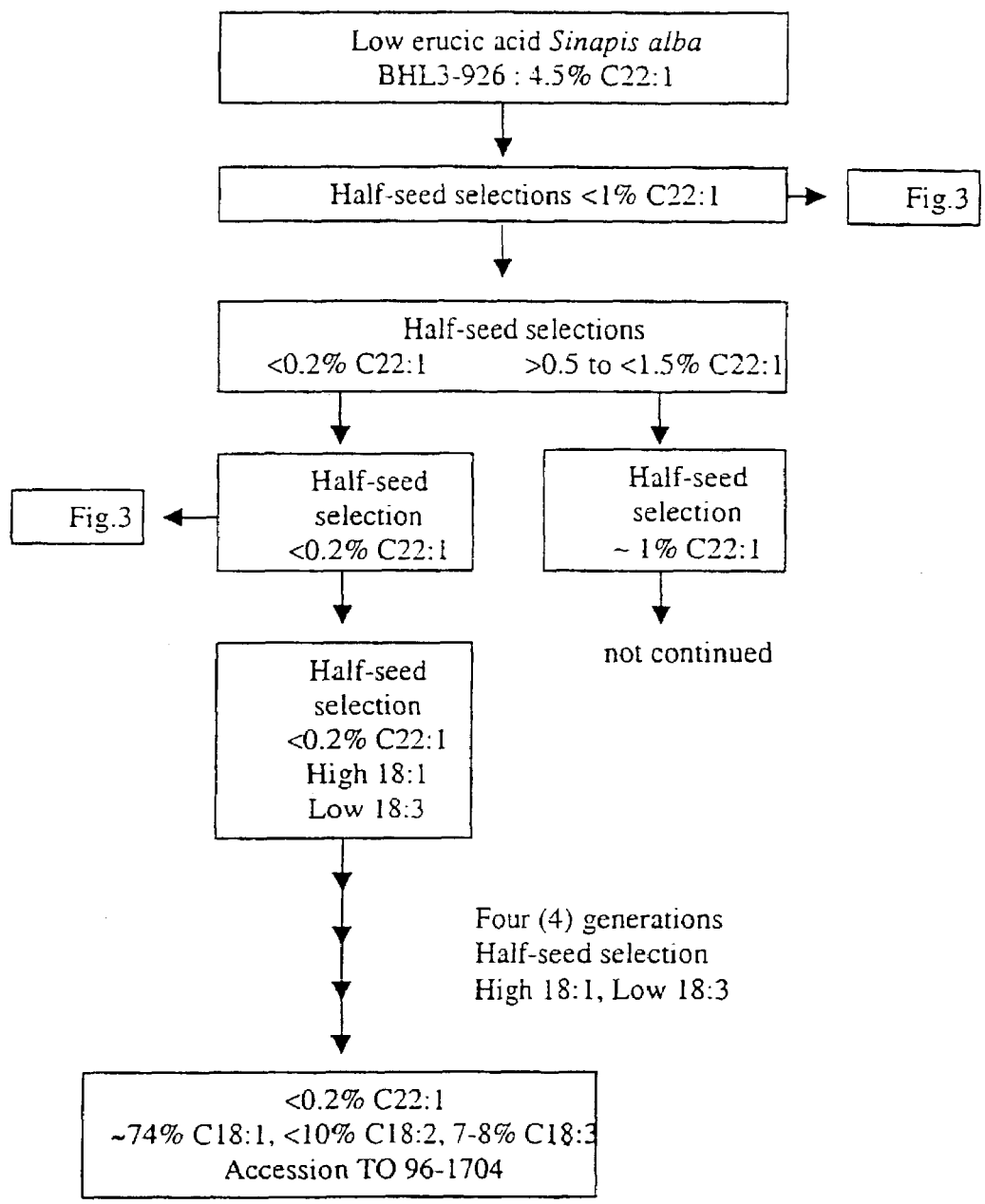
FIG. 1 outlines the development of a low erucic acid, high oleic acid, low linoleic acid, low linolenic acid *S. alba*, for example, but not limited to TO 96-1704 (ATCC-No. PTA 2889) from low erucic acid *S. alba* BHL3-926 (ATCC-No. PTA 2894).

The present invention relates to oil seed, oils and protein meal obtained from *Sinapis alba* L. plants. Furthermore, this invention pertain to *S. alba* plants that produce these oil seed, oils and meal. More particularly, the present invention relates to oil seeds comprising a high oleic acid, low glucosinolate, and either a high or low erucic acid content. The products obtained from these oil seeds are suitable for human and animal consumption, and industrial applications.

The following description is of a preferred embodiment by way of example only and without limitation to the combination of features necessary for carrying the invention into effect.

The present invention provides oilseeds obtained of the species *S. alba* characterized in having a high oleic acid content of about 72 to about 84% by weight. Seeds comprising high oleic acid content are useful for producing edible oils. Furthermore, oilseeds having a low linolenic acid content, for example from about 6-10% by weight are also disclosed. These low levels of linolenic acid enhance the stability of these oils. Oil seeds obtained from *S. alba* plants that comprise high oleic acid, and low linolenic acid may further comprise low levels of p-hydroxybenzyl and benzyl glucosinolate, of less than about 0.1 μmole per g seed, each. These low levels of glucosinolate are desired so that the oil-free meal obtained following extraction of the oil may be used for animal feed or other purposes. Furthermore, the present invention provides for oil seeds having a high level of erucic acid of about 45 to about 65% (by weight), and low levels of p-hydroxybenzyl and benzyl glucosinolate, of less than about 0.1 μmole per g seed, each. Oils having a high erucic acid content are suitable for industrial applications, while the low levels of glucosinolates within the oil seed provides for a meal useful as an animal feed.

By "low erucic acid" (also referred to "substantially zero erucic acid") as used herein, it is meant erucic acid of less than about 0.2% (by weight). Prior art *S. alba* plants having erucic acid of 0.3% or more are referred to as moderately low erucic acid plants, for example those disclosed in Brown et al. (1999) and Raney et al. (1995). The low erucic acid *S. alba* line described in the present invention is a true low erucic acid type with less than 0.2% C22:1 content. The material described in the literature (e.g. Brown et al. 1999; Raney et al. 1995) as "low erucic acid" *S. alba* typically contains from about 0.3% to about 3-4% erucic acid. It has been found that a minor allele is responsible for the low erucic acid contents in *S. alba* as described herein, and this allele has not been disclosed previously (see FIG. 1, which outlines selection of *S. alba* plants comprising the minor allele; "0.2% C22:1").

By "high erucic acid" as used herein, it is meant erucic acid of about 45 to about 65% (by weight), preferably from about 50 to 65% (by weight).

By "low glucosinolate" (also referred to as "substantially free of glucosinolate" or "substantially zero glucosinolate") as used herein, it is meant a p-hydroxybenzyl glucosinolate content of less than or equal to 0.1 μmoles per g of seed and a benzyl glucosinolate of less than or equal to 0.1 μmoles per g of seed. Prior art *S. alba* plants (for example those disclosed in Brown et al. (1999), Krzymanski et al. (1991) and Raney et al. (1995a & 1999b)) contain either p-hydroxybenzyl glucosinolate, benzyl glucosinolate or both in concentrations greater than 0.1 μmoles per g of seed, and are referred to as moderately low glucosinolate plants.

Oils, prepared from oil seeds characterized in having high oleic acid, low erucic acid, and low p-hydroxybenzyl, and benzyl glucosinolate as disclosed herein, meet or exceed the standard established for canola quality oils and canola quality meal. By "canola quality oil" and "canola quality meal" it is meant an oil, or meal, exhibiting the characteristics of oil or meal obtained from canola oil seed. The oil and meal are characterized as having a high oleic acid and low erucic acid content, and a low glucosinolate content (Table 1).

TABLE 1

Characteristics of canola quality oil and meal

| Component | Content |
| --- | --- |
| Canola Oil | |
| Oleic acid | at least 55% by weight |
| Linoleic acid | 16–25% by weight |
| Linolenic acid | 2–13% by weight |
| Erucic acid | less than 2% by weight |
| Canola Meal | |
| Total aliphatic glucosinolate | less than 30 μmole/g oil free meal |

Several of the selection procedures disclosed herein require the testing and propagation of the same seed material. The half-seed method refers to a technique whereby one cotyledon of a seed, for example, *Sinapis alba* or *Brassica*, is used for chemical analysis, while the other cotyledon of the same seed with the attached root can be grown into a plant. Typically the analysis involves determination of fatty acid compositions, for example but not limited to analysis of erucic acid, oleic acid, linoleic acid, linolenic acid, palmitic acid, stearic acid. Traits under embryonic genetic control (e.g., fatty acid contents of *Brassica* and *Sinapis* seed oils), can therefore be directly selected while providing for the propagation of desired seed material.

A rapid screening technique, referred to "Tes-tape" (also known as "Glukotest; Lein, 1970) may be used for determining the glucosinolate content in a few (3 to 6) seeds using glucose sensitive test paper. The technique is well suited to mass screenings and can distinguish high glucosinolate from low glucosinolate seed. The assay of glucose, released from glucosinolates in the presence of myrosinase, provides an indication of the amount of glucosinolates present in the seed. For a more accurate determination of glucosinolate levels, high pressure liquid chromatography or gas chromatography of the trimethylsilyl derivatives may be employed.

A process for the efficient identification and selection of plants, for example but not limited to *S. alba*, comprising substantially low levels of glucosinolate, for example but not limited to p-hydroxybenzyl glucosinolate and benzyl glucosinolate is provided herein. This method is based on the observation that p-hydroxybenzyl and benzyl glucosinolates levels within the leaf or flower buds of a plant, determined using gas chromatography or HPLC, correlate to the level of p-hydroxybenzyl and benzyl glucosinolates within the seed harvested from that plant. Therefore, a rapid selection of plants producing seed that is substantially free of p-hydroxybenzyl glucosinolate, benzyl glucosinolate, or both, may be performed using leaf or flower buds material.

The present invention also pertains to an oilseed of the species *S. alba* bearing an endogenous high oleic acid oil having essentially the composition listed in Table 2.

TABLE 2

Characteristics of high oleic acid oil obtained from *S. alba*

| Component | Content |
| --- | --- |
| Oleic acid | about 72 to about 84% |
| Linoleic acid | less than about 11% |
| Linolenic acid | from about 6 to about 10% |
| Erucic acid | from about 0.0 to about 0.2% |

The high oleic acid oil may further be characterized as comprising a palmitic acid content from about 3 to about 4% by weight, a stearic acid content from about 2% by weight, and a total saturated fatty acid content (C16:0+C18:0+C20:0+C22:0) from about 5.6 to about 6.6% by weight.

Also included within the present invention is a vegetable oil extracted from *S. alba* exhibiting the characteristics defined in Table 2, and plants capable of producing oilseed that exhibit the characteristics defined in Table 2.

An oil seed having essentially the composition defined in Table 2, but being substantially free of p-hydroxybenzyl glucosinolate, and benzyl glucosinolate is also described herein. Furthermore, oil, and meal prepared from such oil seed, and *S. alba* plants capable of producing the oil seed are also disclosed.

It is also to be understood that a high oleic acid oil seed may also be produced, as described herein, characterized by comprising a moderately low erucic acid content of up to about 2% (by weight), rather than the low amount of erucic acid defined in Table 2. Furthermore, oil seed comprising high oleic acid and moderately low erucic acid levels, and that is substantially free of glucosinolate, especially p-hydroxybenzyl and benzyl glucosinolates, is disclosed herein. And oil seed comprising high erucic acid that is substantially free of glucosinolate, especially p-hydroxybenzyl and benzyl glucosinolates may also be produced.

The high content of oleic acid and low concentrations of the linoleic acid and linolenic acid, combined with relatively low contents of saturated fatty acids, provides an oil with excellent nutritional attributes and excellent processing characteristics equal to or superior to those of canola oil available from currently available canola varieties.

Genetically stable *S. alba* plants that develop mature seeds bearing an oil composition essentially as defined in Table 2, for example as exemplified, but not limited to TO 96-1704, may be produced as follows (see FIG. 1):
i) selecting individual seeds with a low erucic acid content. Such seeds may be selected from a moderately low erucic acid *S. alba* line, for example but not limited to BHL3-926. The half-seed technique may be used for fatty acid composition analysis using any suitable methods, for example gas chromatography, and selecting seed with the lowest erucic acid contents;

ii) propagating plants and producing the selected seed by open- or self-pollination;
iii) analyzing fatty acid composition of individual seeds derived from step ii) using the half-seed technique, and selecting genetically stable seed comprising less than 0.2% by weight erucic acid (C22:1);
iv) propagating plants and producing seed by open- or self-pollination;
v) analyzing fatty acid, oleic acid composition in individual seeds and selecting seed with both the highest oleic acid (C18:1) and the lowest linolenic acid (C18:3) contents;
vi) repeating steps iv) and v) as required, for example but not limited to, a further 1 to 6 times, to obtain an oil seed having a high oleic acid content essentially as defined in Table 2.

Plants produced using this method, for example, but not limited to TO 96-1704 (see example 1), do not exhibit increases in palmitic (C16:0) and stearic (C18:0) acid contents, even though the oleic acid content has increased significantly. The fatty acid composition of oil seeds obtained from plants produced using the above method are presented in Table 3. (A more complete listing of the fatty acid profile of oil seeds produced using the above method are presented in Table 4; see also example 1).

TABLE 3

Fatty acid profile of *S. alba* lines prepared using the method outlined in FIG. 1

| *S. alba* generation | Oleic acid | Linoleic acid | Linolenic Acid |
| --- | --- | --- | --- |
| $F_2$ (20 plants) Greenhouse | 69.2 | 10.5 | 12 |
| $F_4$ (49 plants) Greenhouse | 71.5 | 10.1 | 9.7 |
| $F_4$ Field | 72.6 | 10.9 | 7.4 |
| $F_7$ (30 plants) | 74.9 | 8.9 | 8.1 |
| $F_7$ Field | 74.3 | 9.6 | 6.8 |
| Greenhouse* (15 half seeds) | 83.9 | 6.4 | 3.1 |

*seed from T096-1704 plants

Lines prepared using the above method may also be crossed with a high oil *S. alba* line developed by Olsson (1974) to increase the seed oil content and obtain an oil comprising the composition essentially as defined in Table 2.

Figure 2:
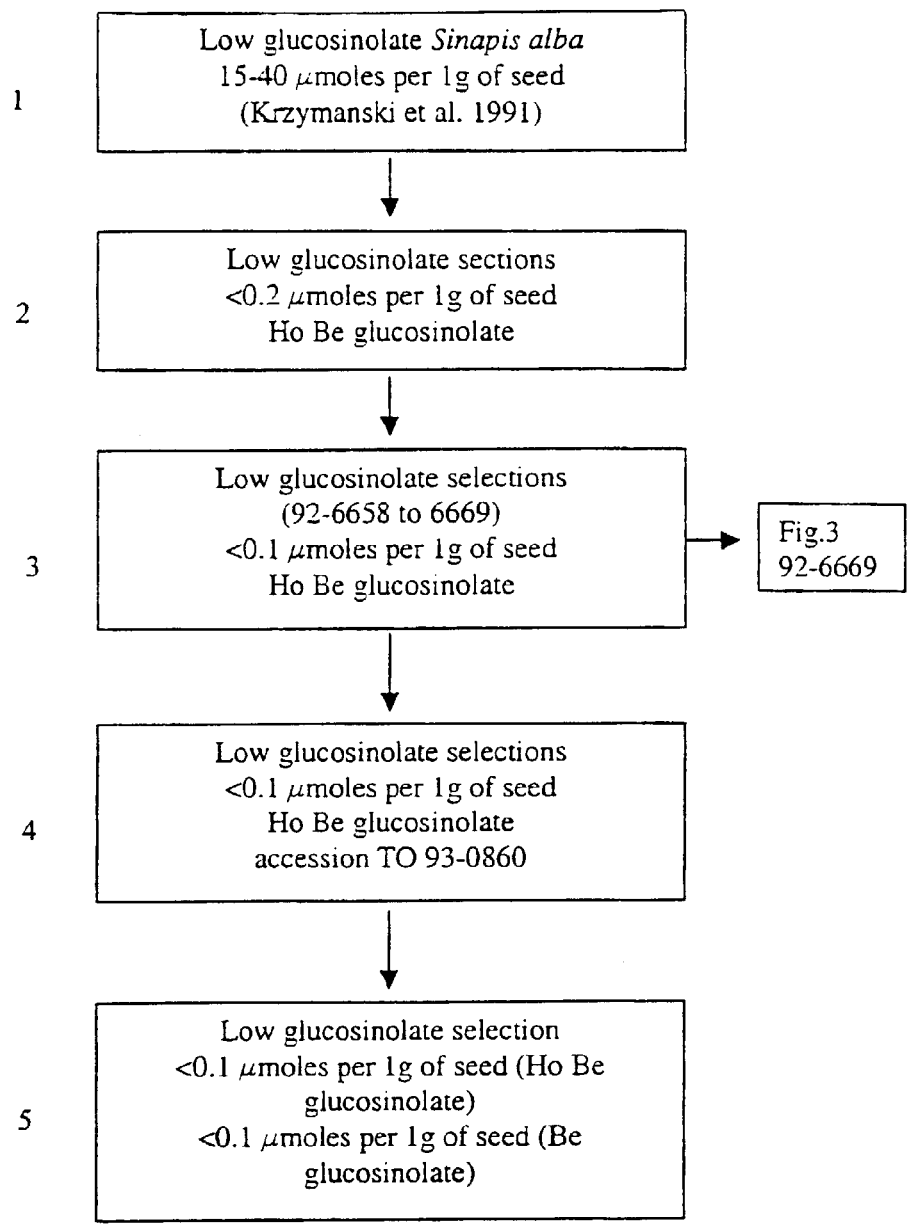
FIG. 2 outlines the development of a low p-hydroxybenzyl glucosinolate *S. alba* (box 4) (for example, but not limited to TO 93-0860; ATCC-No. PTA 289) and low p-hydroxybenzyl glucosinolate (<0.1 µmoles per 1 g of seed)—low benzyl glucosinolate (<0.1 µmoles (per 1 g seed; box 5) from the low glucosinolate *Sinapis alba* population developed by Krzymanski et al. (1991).
Figure 3:
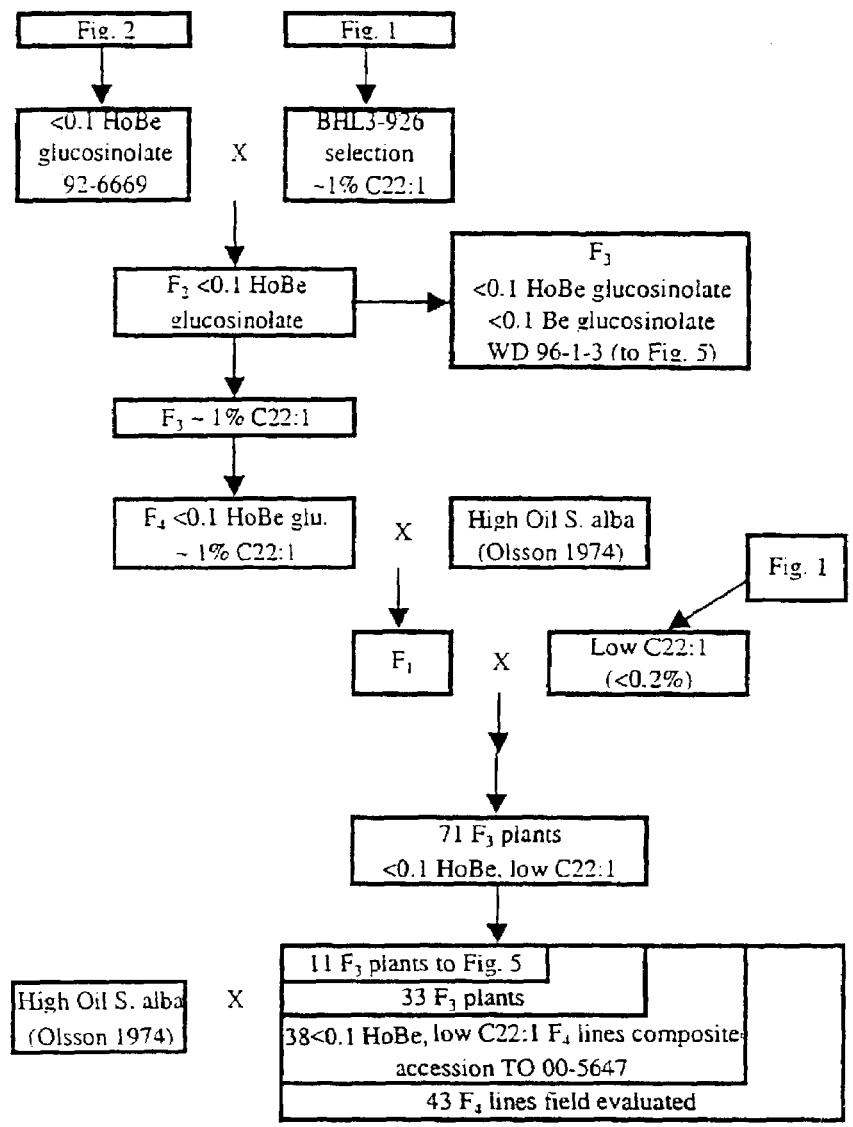
FIG. 3 outlines the development of a low erucic acid, low p-hydroxybenzyl glucosinolate *S. alba*, for example, but not limited to TO 00-5647 (ATCC No. PTA-2890).

Genetically stable *S. alba* plants, for example but not limited to WD 96-1-3, that develop mature seeds comprising low p-hydroxybenzyl glucosinolate, and low benzyl glucosinolate may be produced as follows (see FIGS. 2 and 3):
i) growing plants with a moderately low glucosinolate content. Such plants may be grown from a moderately low glucosinolate *S. alba* line, for example but not limited to that developed by Krzymanski et al. (1991), harvesting open-pollinated seed from individual plants;
ii) identifying plants that produce seed low in p-hydroxybenzyl glucosinolate by analyzing a portion of the seed produced for glucosinolate content and composition, for example, using gas chromatography, and planting remnant seed from selected plants;
iii) growing plants from the seed selected in step ii), and making hand crosses between plants derived from different parent plants to produce crossed seed;
iv) identifying and selecting crossed seed comprising low p-hydroxybenzyl glucosinolate (for example but not limited to 92-6669; FIGS. 2 and 3)
v) growing plants from selected crossed seed of step iv), chain crossing plants, and producing open-pollinated seed on the same plants;

vi) selecting chain crossed seed obtained from open pollinated parent plants that comprise low p-hydroxybenzyl glucosinolate;

vii) growing chain crossed seed derived from crosses between low p-hydroxybenzyl glucosinolate parent plants to produce open-pollinated $F_2$ seed;

viii) growing plants from the $F_2$ population, harvesting plants individually and analyzing open-pollinated seed for glucosinolate content, for example using the Tes-tape method;

ix) selecting seed comprising low p-hydroxybenzyl glucosinolate, as well as low benzyl glucosinolate, for example by gas chromatographic analysis of Tes-tape selected low glucosinolate plants;

x) repeating the cycle of growing and selection (steps viii) and ix)) as required, for example but not limited to 1 to 3 cycles, to obtain a genetically stable *S. alba* line that is substantially free of glucosinolate.

Lines prepared using the above method may also be crossed with a high oil *S. alba* line developed by Olsson (1974) to increase the seed oil content of low glucosinolate *S. alba* comprising the composition as outlined in Table 5 (below).

By crossing plants characterized as having low levels of p-hydroxybenzyl glucosinolate with plants characterized as high oleic acid (e.g. Table 2), genetically stable *S. alba* plants are produced that develop mature seeds containing high oleic acid seed oil moderately low in erucic acid, and after crushing and extraction of oil from the seed, the remaining seed meal is substantially free from p-hydroxybenzyl glucosinolate, or plants that develop mature seeds low in both p-hydroxybenzyl glucosinolate and benzyl glucosinolate (low glucosinolate plants), for example, but not limited to WD96-1-3. This method involves (see FIG. 3):

i) growing a first and second *S. alba* plant:
   a) the first plant characterized by having low p-hydroxybenzyl glucosinolate. Such plants may be obtained, for example, but not limited to, using the method outlined above, or using a variety known to have low p-hydroxybenzyl glucosinolate (e.g. Raney et al., 1995a; Brown et al. 1999);
   b) the second *S. alba* plant known to have moderately low erucic acid (e.g. BHL3-926; Raney et al., 1995a; Brown et al. 1999) and making crosses between the first and second plants to produce crossed seed (FIG. 3);

ii) planting the crossed seed and growing $F_1$ plants and producing open-pollinated $F_2$ seed;

iii) planting the $F_2$ seed, growing and harvesting $F_3$ seed on individual $F_2$ plants separately;

iv) analyzing $F_3$ seed of each $F_2$ plant, or the leaf of the $F_2$ plant, for glucosinolate content and identifying plants having:
   a) both low p-hydroxybenzyl glucosinolate and low benzyl glucosinolate (e.g. WD-96-1-3; FIG. 3);
   a-i) conducting half-seed fatty acid analysis on $F_3$ seed obtained from low p-hydroxybenzyl glucosinolate plants, and selecting seeds having moderately low erucic acid;
   a-ii) growing selected half-seeds into plants and producing $F_4$ seed characterised in comprising low p-hydroxybenzyl glucosinolate, low benzyl glucosinolate and moderately low erucic acid, for example but not limited to WD-96-1-3.

b) or low p-hydroxybenzyl glucosinolate;
   b-i) conducting half-seed fatty acid analysis on $F_3$ seed obtained from low p-hydroxybenzyl glucosinolate plants, and selecting seeds having moderately low erucic acid;
   b-ii) growing selected half-seeds into plants and producing $F_4$ seed characterised in comprising low p-hydroxybenzyl glucosinolate and moderately low erucic acid;

Lines prepared using the above method, comprising low p-hydroxybenzyl glucosinolate and moderately low erucic acid may also be crossed with a high oil *S. alba* line developed by Olsson (1974) to increase the seed oil content and obtain an oil comprising high oleic acid and moderately low erucic acid (see Table 4 and 5).

By crossing plants characterized as having low levels of p-hydroxybenzyl glucosinolate and moderately low erucic acid with plants characterized as low erucic acid, genetically stable *S. alba* plants are produced that develop mature seeds containing high oleic acid seed oil substantially free from erucic acid, and after crushing and extraction of oil from the seed, the remaining seed meal is substantially free from p-hydroxybenzyl glucosinolate, for example but not limited to TO 00-5647 as follows. (see FIG. 3):

i) growing plants from the $F_1$ seed of a cross of low p-hydroxybenzyl glucosinolate, moderately low erucic acid plants with high oil content *S. alba* plants ii) crossing these $F_1$ plants with a low erucic acid plants obtained, for example but not limited to, using the above described method;

iii) growing plants from the $F_1$ seed and harvesting $F_2$ seed;

iv) selecting for low erucic acid and low p-hydroxybenzyl glucosinolate plants by $F_2$ half-seed selection and leaf or bud analysis of selected $F_2$ plants;

v) repeating cycle of crossing and selection, for example but not limited to 1 to 3 times, to obtain a genetically stable *S. alba* plant that comprises low p-hydroxybenzyl glucosinolate and low erucic acid, for example, but not limited to, TO 00-5647.

By crossing plants characterized as having low levels of p-hydroxybenzyl glucosinolate and low erucic acid (TO 00-5647) with plants characterized as low in both p-hydroxybenzyl and benzyl glucosinolate (WD96-1-3), genetically stable *S. alba* plants are produced that develop mature seeds containing high oleic acid seed oil comprising low erucic acid, and after crushing and extraction of oil from the seed, the remaining seed meal is substantially free from p-hydroxybenzyl and benzyl glucosinolate, for example but not limited to TO 00-5648, as follows. (see FIG. 5(A)):

i) growing plants comprising low p-hydroxybenzyl glucosinolate, low erucic acid plants, for example, but not limited to, TO 00-5647;

ii) crossing these plants with plants comprising low p-hydroxybenzyl glucosinolate and low benzyl glucosinolate, for example but not limited to, WD96-1-3;

iii) growing plants from the $F_1$ seed and harvesting $F_2$ seed;

iv) selecting for low erucic acid, low p-hydroxybenzyl and low benzyl glucosinolate plants, for example using $F_2$ half-seed selection, or leaf or bud analysis of selected $F_2$ plants;

v) repeating cycle of crossing and selection, for example but not limited to 1 to 3 times, to obtain a genetically stable *S. alba* plant that comprises low p-hydroxybenzyl glucosinolate, low benzyl glucosinolate, and low erucic acid, for example, but not limited to, TO 00-5648.

Lines prepared using the above method, comprising low p-hydroxybenzyl, low benzyl, or both low p-hydroxybenzyl and low benzyl glucosinolate may also be crossed with a high oil *S. alba* line developed by Olsson (1974) to increase the seed oil content and obtain an oil comprising the composition essentially as defined in Tables 4 and 5 (below).

Figure 4:
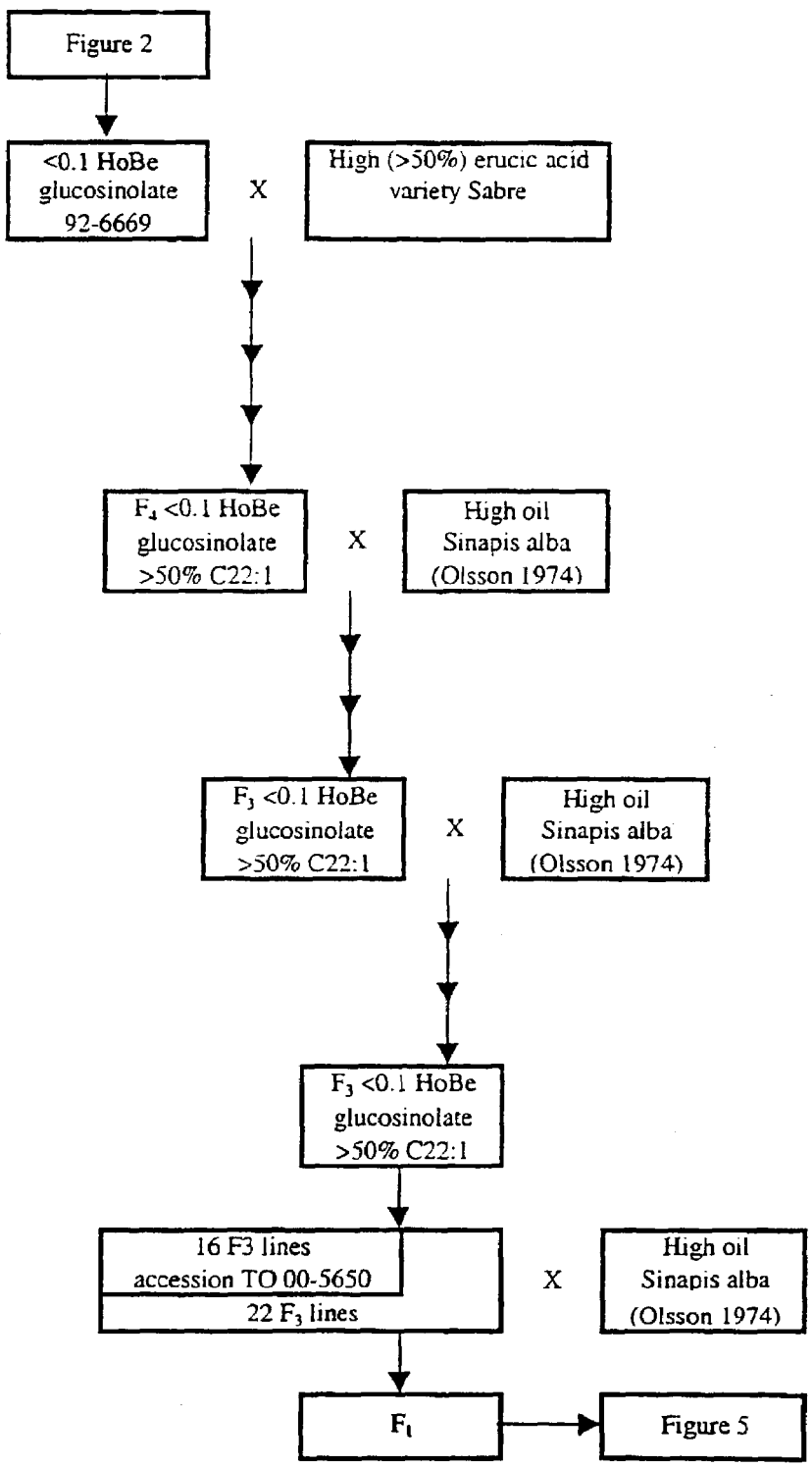
FIG. 4 outlines the development of a high erucic acid, low p-hydroxybenzyl glucosinolate *S. alba*, for example, but not limited to TO 00-5650 (ATCC No. PTA 2893).

Genetically stable *S. alba* plants, for example, but not limited to TO 00-5649 or TO 00-5650, that develop mature seeds containing seed oil with a concentration of erucic acid (of at least about 45% C22:1 by weight) in which the remaining seed meal, after crushing and extraction of oil from the seed, is basically free from glucosinolate, for example but not limited to p-hydroxybenzyl glucosinolate (less than about 0.1 μmoles per g of seed) may be produced as follows (see FIGS. 4 and 5(B)):

i) growing:
  a) low p-hydroxybenzyl glucosinolate, low benzyl glucosinolate plants; and
  b) a high erucic acid (at least about 50% C22:1 by weight), for example, but not limited to the variety Sabre;
ii) making crosses between plants of the two genotypes, producing crossed seed, planting and producing plants;
iii) identifying plants comprising low p-hydroxybenzyl glucosinolate and low benzyl glucosinolate (low glucosinolate plants), conducting half-seed fatty acid analysis on $F_3$ seed obtained from low glucosinolate plants, and selecting and growing high erucic acid half-seeds into plants and producing $F_4$ seed by self- and open-pollination;
iv) repeating step iii) as required to produce a genetically stable, true breeding line of *S. alba* that produces seed characterized in having a high erucic acid content, and in which the remaining oil free meal, after oil extraction, is basically free from glucosinolates, for example but not limited to, p-hydroxybenzyl glucosinolate and benzyl glucosinolate (each less than about 0.1 μmoles per 1 g of seed), for example, but not limited to TO 00-5649 ore TO 00-5650 (FIGS. 4 and 5(B); Table 5);

This line may be crossed with a high oil content *S. alba* line, such as the high oil content *S. alba* line developed by Olsson (1974), followed by re-selection of the high erucic acid, and low p-hydroxybenzyl glucosinolate, low benzyl glucosinolate, or both, traits to produce an oil seed having a high erucic acid, low glucosinolate (either p-hydroxybenzyl, benzyl, or both p-hydroxybenzyl and benzyl glucosinolate), and high oleic acid composition. The development of *S. alba* with high erucic acid content is useful as an industrial oil. Furthermore, the oil free seed meal that is essentially free from glucosinolates may be used as a high protein animal feed.

A summary of the fatty acid composition determined from *S. alba* lines produced by the above methods is provided in Table 4. The fatty acid profile of other plants (*S. alba*, and *B. napus*) is also included in Table 4.

TABLE 4

Fatty acid composition of *Sinapis alba* lines as described herein, compared to *S. alba* (WD 96-1-3; High Oil; Sabre; AC Pennant), and *Brassica napus* canola variety AC Excel.

| Line* | Fatty Acid Composition | | | | | | | | | |
|---|---|---|---|---|---|---|---|---|---|---|
| | C16:0 | C16:1 | C18:0 | C18:1 | C18:2 | C18:3 | C20:0 | C20:1 | C22:0 | C22:1 |
| BHL 3-926 | 4.3 | 0.3 | 1.8 | 61.9 | 13.1 | 11.8 | 0.5 | 2.9 | 0.2 | 1.1 |
| TO 96-1704 | 3.9 | 0.3 | 1.8 | 73.7 | 9.2 | 7.8 | 0.5 | 1.2 | 0.2 | 0.1 |
| TO 93-0860 | 3.2 | 0.3 | 1.0 | 34.3 | 10.0 | 11.9 | 0.5 | 11.0 | 0.3 | 23.5 |
| TO 00-5647 | 3.9 | 0.3 | 1.4 | 69.9 | 11.0 | 10.1 | 0.4 | 1.1 | 0.2 | 0.1 |
| TO 00-5648 | 3.6 | 0.3 | 1.7 | 68.8 | 8.6 | 12.8 | 0.5 | 1.3 | 0.2 | 0.2 |
| TO 00-5650 | 2.0 | 0.2 | 0.6 | 13.8 | 6.7 | 10.7 | 0.5 | 5.4 | 0.5 | 53.8 |
| TO 00-5649 | 2.2 | 0.2 | 0.7 | 19.2 | 7.0 | 9.2 | 0.5 | 7.8 | 0.5 | 46.8 |
| WD 96-1-3 | 4.7 | 1.1 | 3.3 | 43.2 | 18.6 | 14.7 | 0.9 | 2.9 | 0.5 | 1.4 |
| High Oil | 2.5 | 0.3 | 0.8 | 23.8 | 8.8 | 7.3 | 0.6 | 9.1 | 0.5 | 41.3 |
| Sabre | 2.2 | 0.2 | 0.6 | 15.0 | 8.8 | 8.4 | 0.5 | 6.3 | 0.7 | 51.4 |
| AC Pennant | 2.6 | 0.2 | 1.0 | 25.0 | 8.4 | 10.7 | 0.7 | 10.6 | 0.5 | 36.3 |
| AC Excel (*B. napus*) | 3.5 | 0.2 | 1.8 | 68.1 | 16.0 | 7.0 | 0.6 | 1.4 | 0.4 | 0.1 |

*BHL 3-926 low erucic acid base population after one generation for low erucic acid content selection (ATCC No. PTA-2894, deposit date Dec. 20, 2000)
TO 96-1704 low erucic acid, high oleic acid, low linoleic acid, low linolenic acid line (ATCC No. PTA-2889; deposit date Dec. 20, 2000)
TO 93-0860 normal erucic acid, low p-hydroxybenzyl glucosinolate line (ATCC No. PTA-2895; deposit date Dec. 20, 2000)
TO 00-5647 low erucic acid, high oleic acid, low p-hydroxybenzyl glucosinolate (ATCC No. PTA-2890; deposit date Dec. 20, 2000)
TO 00-5648 low erucic acid, low p-hydroxybenzyl glucosinolate, zero benzyl glucosinolate line (ATCC No. PTA-2891;deposit date Dec. 20, 2000)
TO 00-5650 high erucic acid, low p-hydroxybenzyl glucosinolate line (ATCC No. PTA-2893;deposit date Dec. 20, 2000)
TO 00-5649 > 45% erucic acid, low p-hydroxybenzyl glucosinolate, low benzyl glucosinolate (ATCC No. PTA-2892;deposit date Dec. 20, 2000)
WD 96-1-3 moderately low erucic acid, low p-hydroxybenzyl glucosinolate, zero benzyl glucosinolate line
High Oil high oil content line (Olsson 1974)
Sabre high erucic acid *Sinapis alba* variety
AC Pennant condiment *Sinapis alba* variety
AC Excel (*B. napus*) canola-quality *Brassica napus* variety A summary of glucosinolate compositions and total glucosinolate contents determined from S. alba lines produced by the above methods is provided in Table 5. The glucosinolate content of other plants (S. alba, and B. napus) is also included in Table 5.

TABLE 5

Glucosinolate content of Sinapis alba lines as described herein, compared to S. alba (WD 96-1-3; High Oil; Sabre; AC Pennant), and Brassica napus canola variety AC Excel

| | Glucosinolate content (μmoles per g seed)* | | | | | |
|---|---|---|---|---|---|---|
| Line | HOBut | HOBenzyl | HOBenzyl | Aliphatic | Indolyl | Total |
| BHL-3-926 | 3.4 | 0.1 | 161 | 3.4 | 1.2 | 166.1 |
| TO96-1704 | 1.8 | 0.1 | 163.3 | 1.8 | 2.2 | 167.8 |
| TO93-0860 | 22.6 | 2.2 | 0 | 23.4 | 3.9 | 29.9 |
| TO00-5647 | 25.1 | 9.1 | 0 | 26.3 | 15.3 | 51.5 |
| TO00-5648 | 12.6 | 0 | 0.1 | 12.8 | 6.7 | 20.1 |
| TO00-5649 | 42 | 0 | 0 | 42.9 | 8.5 | 52.7 |
| TO00-5650 | 15.9 | 15.4 | 0 | 16.5 | 11.9 | 44.3 |
| WD96-1-3 | 14.2 | 0 | 0 | 15.1 | 7.5 | 24.1 |
| High Oil | 1.3 | 0.5 | 168.4 | 1.3 | 1 | 172.8 |
| Sabre | 4.4 | 0 | 195.6 | 4.4 | 0.6 | 203.1 |
| AC Pennant | 3.5 | 0 | 146.2 | 3.5 | 0.3 | 151.5 |
| AC Excel | 3.4 | 0 | 0 | 6 | 3.6 | 9.8 |

HOBut: 2-hydroxy-3-butenyl glucosinolate
Benzyl: Benzyl glucosinolate
HOBenzyl: p-hydroxybenzyl glucosinolate
Aliphatic: Total aliphatic glucosinolate content including allyl, 3-butenyl, 4-pentenyl, 2-hydroxy-3-butentyl and 2-hydroxy-4-pentenyl glucosinolates
Indolyl: Total indolyl glucosinolate content, includes indolyl-3-methyl glucosinolate and 4-hydroxyindolyl-3-methyl glucosinolate
Total: Total glucosinolate content of seed The following seeds have been deposited with the ACTT on Dec. 20, 2000:

BHL 3-926 (a low erucic acid base population) ATCC No. PTA-2894;
TO 96-1704 (a low erucic acid, high oleic acid, low linoleic acid, low linolenic acid line) ATCC No. PTA-2889;
TO 93-0860 (a normal erucic acid, low p-hydroxybenzyl glucosinolate line) ATCC No. PTA-2895;
TO 00-5647 (a low erucic acid, high oleic acid, low p-hydroxybenzyl glucosinolate line) ATCC No. PTA-2890;
TO 00-5648 (a low erucic acid, low p-hydroxybenzyl glucosinolate, low benzyl glucosinolate line) ATCC No. PTA-2891;
TO 00-5650 (a high erucic acid, low p-hydroxybenzyl glucosinolate line) ATCC No. PTA-2893;
TO 00-5649 (a high erucic acid, low p-hydroxybenzyl glucosinolate, low benzyl glucosinolate) ATCC No. PTA-2892.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

EXAMPLES

Example 1

Selection for High Oleic Acid Low Linolenic Acid Low Erucic Acid S. alba. (see FIG. 1)

At each generation, selection pressure was applied for a high oleic and low linolenic fatty acid profile. All selections were based on half-seed analysis. The selections were then confirmed by analysis of a five, ten or fifty seed "bulk" analysis of seed produced on the plants grown from selected half-seeds. Growth of the plants in the greenhouse or growth chambers followed standard greenhouse practices. Open pollinated seed was produced by brush pollination of selected plants grown in isolation. Selfed seed was produced by bud pollination. During two different growth seasons, bulk composites of selected lines of all six generations of low erucic acid (less than about 0.2% by weight) S. alba were grown at a farm site as 1 meter by 6 meter plots under isolation tents to prevent cross pollination between lines and with other lines of S. alba.

Figure 6:
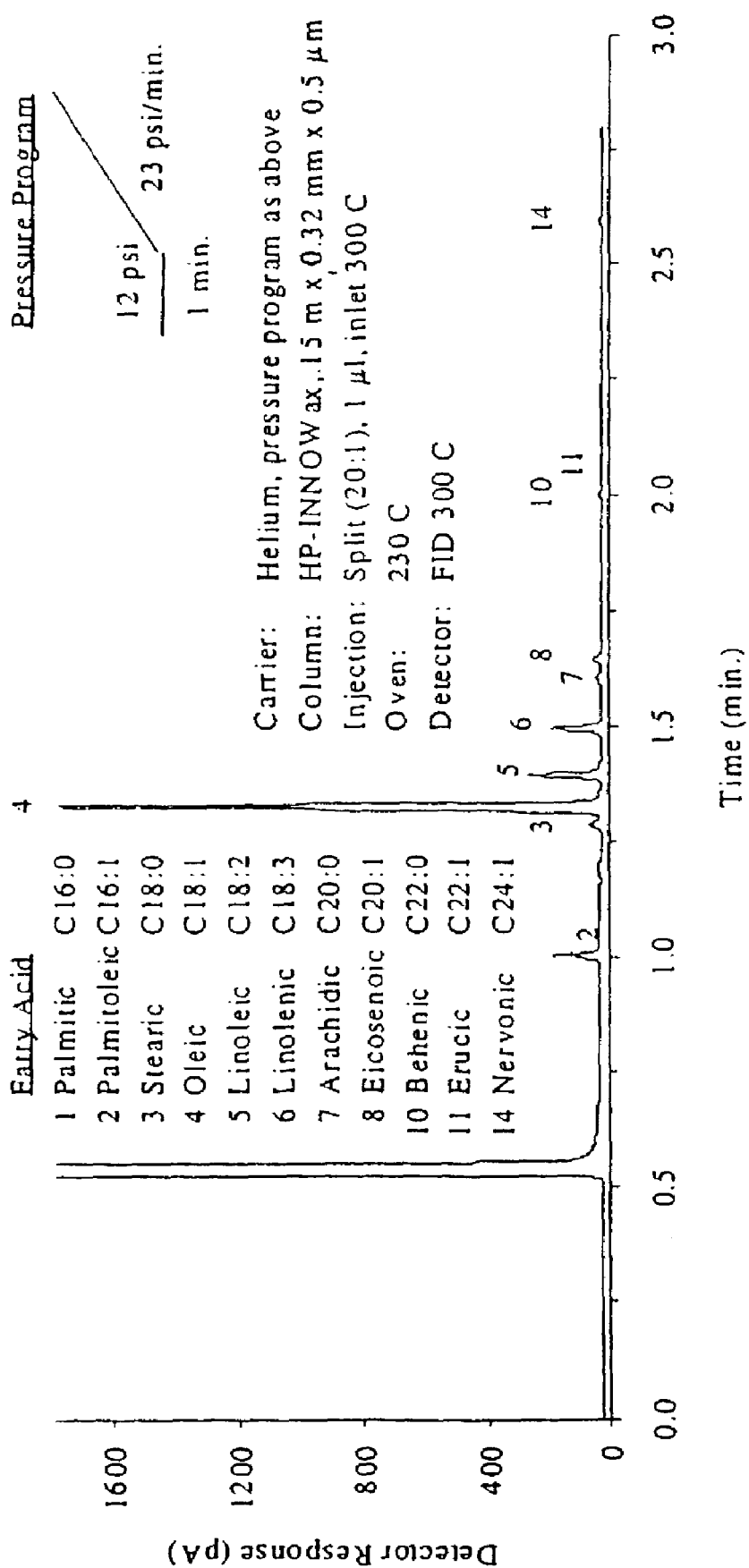
FIG. 6 shows a gas chromatogram of fatty acid methyl-esters of seed oil obtained from TO 96-1704 (ATCC No. PTA 2889 see FIG. 1).

The fatty acid composition of bulk seed samples and germinated seeds (18 hours at RT) was determined as follows. The oil of 'bulk' samples (up to 2 grams) was first extracted by shaking the seed, a metal rod and hexane together in a 20 ml PET scintillation vial in a reciprocating shaker. An appropriate amount of oil and solvent was then transferred to an autosampler vial. Transesterification was accomplished in 0.1 ml 0.8% sodium metal in methanol and 0.05 ml heptane for 20 minutes at RT. After removal from the inner coytyledon and radical, the outer cotyledon of germinated seeds was transesterified by grinding it with a glass rod in a 1.5 ml autosampler vial in the presence of transesterification reagent. The inner cotyledon with radical attached is still viable and potentially can be grown to maturity depending on the results of the gas chromatographic analysis of the outer cotyledon. After transesterification of either the 'bulk' samples or the outer cotyledons, 0.1 ml of 0.2 M sodium phosphate, pH 7.0 was added to vial and the sample briefly dried under a stream of air (1 minute) and 0.5 ml of heptane added. Chromatography of the fatty acid methyl esters was performed with a Hewlett Packard 6890 gas chromatograph as described in FIG. 6.

A moderately low erucic acid (<5%) parent line (BHL-926) was half-seed selected for lowest possible erucic acid content (16 out of 272 with <1%). From the bulk analysis of the open pollenated seed, the 6 lines of the 16 were separated into two groups. Group 1 averaged 0.4% erucic acid and group 2 averaged 1.4% erucic acid. Half-seed selection was carried out on each of the two groups (20 seeds from each plant). Plants of group 1 segregated seeds that contained low or no erucic acid by our analysis. Plants of group 2 did not segregate low erucic acid half-seeds. The selected low or moderately low erucic acid half-seed progeny from each of the two groups were grown in isolation in the greenhouse and open pollenated $F_2$ seed harvested.

Upon half-seed analysis of harvested seed of group 1, plants were found to be all 0 to 0.2% erucic acid, whereas seed from group 2 plants was found to contain between 1% and 5% erucic acid. Therefore, group 2 plants were discontinued. Selected half-seeds from group 1 contained oleic acid contents between 67% and 71%. Selected plants (n=54) were bud selfed and $F_3$ seed harvested. Based on the 'bulk' analysis, 17 lines were selected for continuation by half-seed selection (12 seeds analyzed per line). Selected half-seeds (52) contained between 70% and 77% oleic acid. Selected plants were bud selfed and $F_4$ seed harvested. The seed from 16 lines was bulked together and grown at the farm site. The bulked $F_4$ seed was also half-seed selected and ten seeds out of 30 were selected with oleic acid contents between 70% and 80%.

Bulk analysis of $F_5$ seed from nine lines harvested revealed that actual oleic acid content ranged between 70% and 76%. Three lines were selected for continuation. 48 seeds of each were analyzed and a total of 45 seeds selected Bulk analysis of $F_6$ seed from 26 lines revealed nine lines with >78% oleic acid. 24 half-seeds from each of these nine lines were analyzed and 30 selected for selfing. Composites from all plants grown at each generation were made and these were grown at the farm site in isolation tents. The fatty acid composition of the seed grown from these composites is shown in Table 6.

The results indicate that selection for higher oleic acid (C18:1) contents was successful. At the same time selection for a lower content of linolenic acid (C18:3) and low erucic acid (C22:1) was also successful. The oleic acid content was elevated at least 5%, the linolenic acid content lowered by 3%, and erucic acid content reduced to 0.1% or less. The fatty acid profile of field grown TO96-1704 is characterized as comprising oleic acid of 74.3 to 74.9% (by weight; C18:1), linolenic acid of 6.8 to 8.1% (by weight; C18:3), and erucic acid of 0.1% (by weight; C22:1).

TABLE 6

Fatty acid profiles of six generations of selection for high oleic acid and parental lines

| Line | Gen. | Year | C16:0 | C16:1 | C18:0 | C18:1 | C18:2 | C18:3 | C20:0 | C20:1 | C22:0 | C22:1 |
|---|---|---|---|---|---|---|---|---|---|---|---|---|
| BHL-926[1] | Parent | GH | 3.6 | 0.3 | 1.8 | 57.3 | 11.8 | 13.6 | 0.5 | 6.2 | 0.3 | 4.5 |
| Group1[1] | $F_1$ | GH | 5.1 | 0.5 | 1.7 | 58.9 | 17.1 | 13.6 | 0.5 | 1.7 | 0.3 | 0.4 |
| Group 2[1] | $F_1$ | GH | 4.9 | 0.5 | 1.9 | 58.1 | 15.9 | 13.0 | 0.6 | 3.4 | 0.3 | 1.4 |
| TO93-0876[2] | $F_2$ | 1996 | 3.7 | 0.2 | 1.9 | 69.2 | 10.5 | 12.0 | 0.5 | 1.1 | 0.2 | 0.0 |
|  |  | 1998 | 4.1 | 0.3 | 1.9 | 68.7 | 12.2 | 9.1 | 0.6 | 1.2 | 0.3 | 0.1 |
| TO96-1700[2] | $F_3$ | 1996 | 3.7 | 0.2 | 1.8 | 71.3 | 9.8 | 10.7 | 0.5 | 1.1 | 0.2 | 0.1 |
|  |  | 1998 | 4.2 | 0.3 | 1.9 | 70.1 | 11.6 | 8.3 | 0.6 | 1.3 | 0.3 | 0.1 |
| TO96-1701[2] | $F_4$ | 1996 | 3.9 | 0.3 | 1.9 | 71.6 | 10.1 | 9.7 | 0.5 | 1.1 | 0.2 | 0.0 |
|  |  | 1998 | 4.2 | 0.3 | 1.9 | 72.6 | 10.2 | 7.4 | 0.5 | 1.2 | 0.2 | 0.0 |
| TO96-1702[2] | $F_5$ | 1996 | 3.8 | 0.3 | 1.7 | 74.3 | 9.1 | 8.6 | 0.4 | 1.0 | 0.2 | 0.0 |
|  |  | 1998 | 4.1 | 0.3 | 1.6 | 71.8 | 10.2 | 7.7 | 0.5 | 1.6 | 0.2 | 1.0 |
| TO96-1703[2] | $F_6$ | 1996 | 3.7 | 0.3 | 2.0 | 74.7 | 8.9 | 8.0 | 0.5 | 1.0 | 0.2 | 0.0 |
|  |  | 1998 | 4.2 | 0.3 | 1.8 | 73.9 | 10.0 | 6.8 | 0.5 | 1.2 | 0.2 | 0.1 |
| TO96-1704[2] | $F_7$ | 1996 | 3.7 | 0.3 | 1.9 | 74.9 | 8.9 | 8.1 | 0.5 | 1.0 | 0.2 | 0.1 |
|  |  | 1998 | 4.1 | 0.3 | 1.7 | 74.3 | 9.6 | 6.8 | 0.5 | 1.2 | 0.2 | 0.1 |

[1]Bulk analysis of greenhouse produced seed.
[2]Bulk analysis (400 seeds) of seed produced in 1996 and 1998 in isolation tents.

Characterization of the fatty acid profile of seeds obtained from green house grown TO 96-1704 plants is presented in Table 7. Under these conditions, oil seed obtained from these plants comprise up to 84% (average 82.5%; by weight) oleic acid and 0.0% erucic acid. Similar analysis of plants grown under field conditions is presented in Table 8. Oil seed grown in the filed field exhibit oleic acid contents of up to 79.7% (average 78.0%; by weight) and 0 to 0.1% (by weight) erucic acid.

TABLE 7

Fatty Acid Composition of 15 Half-Seeds of *Sinapis alba* Line TO 96-1704 ($F_6$ seed of $F_5$ plants) Grown in the Greenhouse Fatty Acid Composition (% by weight)

| Plant # | C16:0 | C16:1 | C18:0 | C18:1 | C18:2 | C18:3 | C20:0 | C20:1 | C22:0 | C22:1 |
|---|---|---|---|---|---|---|---|---|---|---|
| TO95-1303-5 | 5.1 | 0 | 0.9 | 82.5 | 7.6 | 3.8 | 0.1 | 0 | 0 | 0 |
| TO95-1302-2 | 5.4 | 0 | 0.3 | 83.0 | 6.9 | 3.1 | 0 | 1.3 | 0 | 0 |
| TO95-1303-2 | 4.7 | 0 | 1.6 | 82.1 | 7.6 | 3.9 | 0 | 0.2 | 0 | 0 |
| TO95-1303-2 | 4.7 | 0 | 1.4 | 83.9 | 6.4 | 3.1 | 0 | 0.5 | 0 | 0 |
| TO95-1303-5 | 5.1 | 0 | 0.9 | 82.5 | 6.9 | 3.5 | 0.1 | 0.9 | 0 | 0 |
| TO95-1303-5 | 4.9 | 0 | 0.9 | 83.3 | 7.4 | 2.9 | 0 | 0.8 | 0 | 0 |
| TO95-1303-5 | 4.9 | 0 | 1.1 | 82.8 | 6.8 | 3.8 | 0 | 0.6 | 0 | 0 |
| TO95-1303-5 | 4.9 | 0 | 0.8 | 82.5 | 7.6 | 3.6 | 0 | 0.7 | 0 | 0 |
| TO95-1304-1 | 4.7 | 0 | 1.9 | 82.5 | 7.0 | 3.4 | 0 | 0.5 | 0 | 0 |
| TO95-1304-1 | 4.9 | 0 | 1.2 | 82.4 | 7.2 | 4.0 | 0 | 0.3 | 0 | 0 |
| TO95-1304-7 | 5.0 | 0 | 1.0 | 81.8 | 7.2 | 4.2 | 0 | 0.9 | 0 | 0 |
| TO95-1303-1 | 5.2 | 0 | 0.8 | 81.9 | 7.8 | 3.5 | 0 | 0.8 | 0 | 0 |
| TO95-1303-1 | 5.2 | 0 | 0.8 | 82.0 | 8.2 | 3.1 | 0 | 0.7 | 0 | 0 |
| TO95-1303-1 | 5.0 | 0 | 1.0 | 81.8 | 7.2 | 4.1 | 0 | 1.0 | 0 | 0 |
| TO95-1303-1 | 5.0 | 0 | 0.6 | 82.1 | 7.6 | 3.5 | 0 | 0.5 | 0 | 0 |
| Average | 5.0 | 0 | 1.0 | 82.5 | 7.3 | 3.6 | 0 | 0.7 | 0 | 0 |

TABLE 8

Fatty Acid Composition of 15
Half-Seeds of *Sinapis alba* Line TO 96-1704 Grown in the Field at Saskatoon

| | Fatty Acid Composition (% by weight) | | | | | | | | | |
|---|---|---|---|---|---|---|---|---|---|---|
| Plant # | C16:0 | C16:1 | C18:0 | C18:1 | C18:2 | C18:3 | C20:0 | C20:1 | C22:0 | C22:1 |
| 1704-1 | 38 | 0.4 | 1.3 | 79.7 | 7.3 | 4.5 | 0.3 | 1.2 | 0.2 | 0.1 |
| 1704-2 | 3.2 | 0.2 | 1.0 | 79.7 | 6.8 | 6.8 | 0.3 | 1.4 | 0.1 | 0 |
| 1704-3 | 3.6 | 0.3 | 1.7 | 78.9 | 6.8 | 5.5 | 0.4 | 1.1 | 0.2 | 0.1 |
| 1704-4 | 3.5 | 0.2 | 1.1 | 78.9 | 8.3 | 6.5 | 0.3 | 1.2 | 0 | 0 |
| 1704-5 | 3.5 | 0.3 | 1.6 | 78.3 | 6.8 | 7.0 | 0.4 | 1.1 | 0.2 | 0 |
| 1704-6 | 3.8 | 0 | 1.3 | 78.0 | 8.6 | 6.6 | 0.4 | 1.3 | 0 | 0 |
| 1704-7 | 3.6 | 0.2 | 1.4 | 77.8 | 8.5 | 6.3 | 0.4 | 1.3 | 0.2 | 0 |
| 1704-8 | 3.8 | 0.4 | 1.4 | 77.8 | 8.7 | 5.3 | 0.3 | 1.1 | 0.1 | 0.1 |
| 1704-9 | 3.6 | 0.4 | 1.5 | 77.7 | 7.6 | 6.0 | 0.4 | 1.2 | 0.2 | 0.1 |
| 704-10 | 3.8 | 0 | 1.3 | 77.6 | 8.6 | 5.4 | 0.3 | 1.2 | 0 | 0 |
| 704-11 | 3.7 | 0.2 | 1.2 | 77.6 | 8.7 | 6.9 | 0.3 | 1.1 | 0.1 | 0 |
| 704-12 | 3.5 | 0.3 | 1.6 | 77.2 | 8.2 | 6.5 | 0.4 | 1.1 | 0.2 | 0 |
| 704-13 | 3.9 | 0.4 | 1.5 | 77.1 | 7.8 | 5.5 | 0.4 | 1.2 | 0.2 | 0.1 |
| 704-14 | 4.0 | 0.5 | 1.6 | 77.0 | 8.0 | 6.2 | 0.4 | 1.0 | 0.2 | 0 |
| 704-15 | 3.7 | 0.2 | 1.8 | 76.9 | 7.9 | 7.5 | 0.4 | 1.0 | 0.2 | 0 |
| Average | 3.7 | 0.3 | 1.4 | 78.0 | 7.9 | 6.2 | 0.4 | 1.2 | 0.1 | 0 |

Example 2

Selection for *Sinapis alba* Substantially Free of
p-hydroxybenzyl and Benzyl Glucosinolate

*Sinapis alba* lines free from p-hydroxybenzyl and benzyl glucosinolates, according to the present invention, can be created through selections from the moderately low glucosinolate *S. alba* population developed by Krzymanski et al. (1991). The mutation affecting p-hydroxybenzyl and benzyl glucosinolate contents is such that only trace amounts of p-hydroxybenzyl and benzyl glucosinolates (<0.1 µmoles per 1 g of seed) are formed in the homozygous recessive condition. The low p-hydroxybenzyl glucosinolate seeds may be selected using any suitable analytical technique, for example gas chromatography.

*S. alba* plants free from p-hydroxybenzyl glucosinolate, can synthesize and accumulate benzyl glucosinolate in their seed. Benzyl glucosinolate is not found in *S. alba* condiment mustard high in p-hydroxybenzyl glucosinolate. The use of benzyl glucosinolate as an internal standard in established gas chromatographic determination of glucosinolate prevents the identification of benzyl glucosinolate containing *S. alba* plants. Therefore, allyl glucosinolate was used as an internal standard for gas chromatography of glucosinolates.

Figure 7:
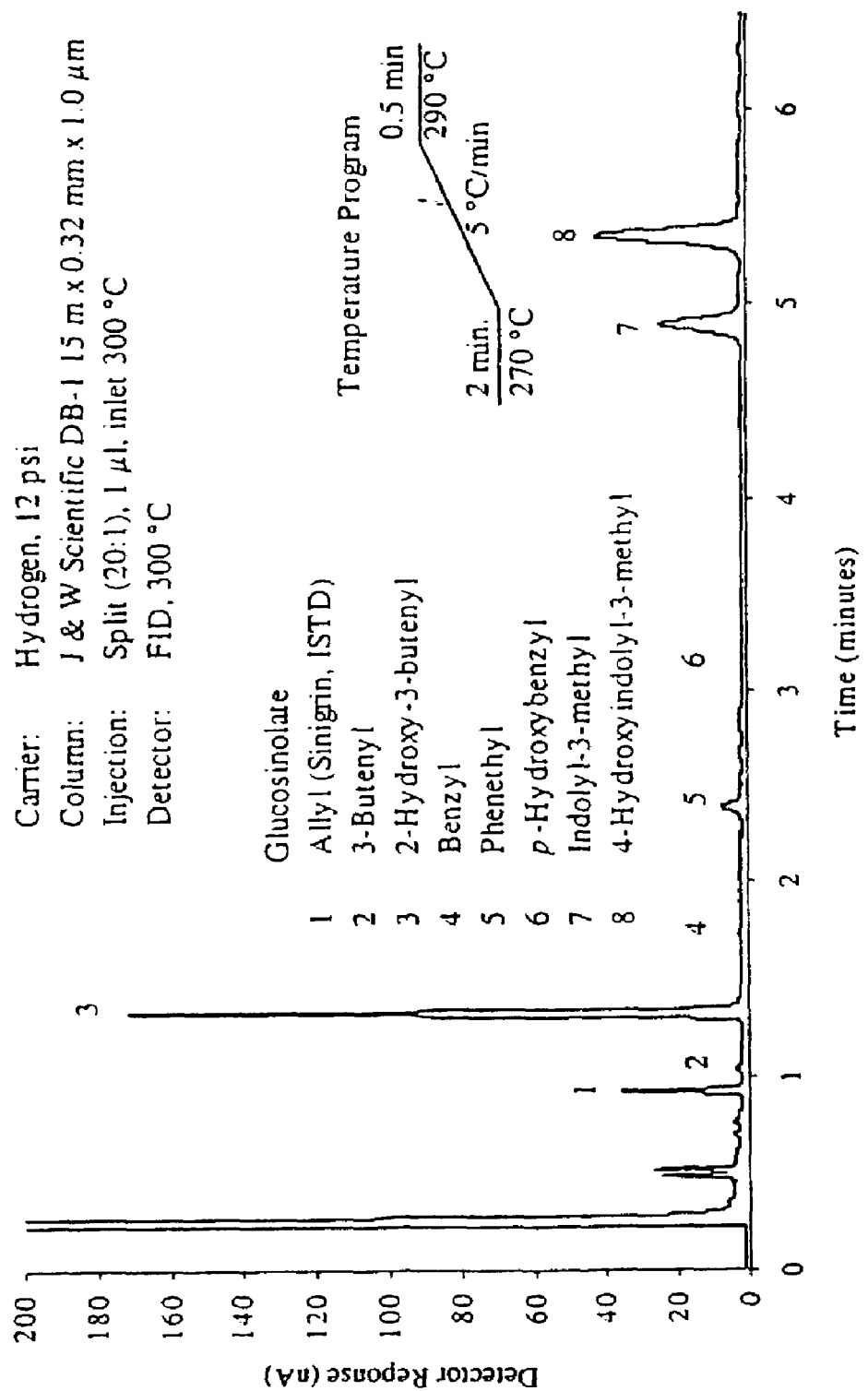
FIG. 7 shows a Gas chromatogram of glucosinolate trimethylsilyl derivatives obtained from the low erucic acid, low glucosinolate line TO00-5648 (ATCC No. PTA 2891).

The glucosinolate content of seed was determined by the gas chromatographic method of Thies (1980) with certain modifications. The procedure (TMS analysis) was as follows: 0.5 gram of seed was placed in plastic 7 ml scintillation vials each containing a 25 mm by 8 mm stainless steel rod. 2 ml of methanol, 1 ml of 1 mM sinigrin and 0.1 ml of 0.6 M barium and lead acetate were then added and the vials capped. The vials were then shaken on an Eberbach reciporating shaker (37 mm stroke, 280 strokes per minute) for 30 minutes to 1 hour in order to pulerize the seed and extract the glucosinolate. The vials were then centrifuged and the supernatant decanted onto 0.15 ml of preswollen DEAE-Sephadex A-25 in Bio-Rad microcolumns. These columns were then washed with 1.8 ml 67% methanol, 1.8 ml water, and 1 ml 0.02M pyridine-acetic acid buffer, pH 5.5 to remove unbound substances. Then 0.05 ml of aryl sulfatase solution is added to specifically release the glucosinolates from the DEAE-Sephadex by cleavage of their sulfate moiety. After overnight incubation with the enzyme, the glucosinolate were eluted into 1.5 ml Hewlett-Packard autosampler vials with 1.5 ml water. The water was evaporated under a stream of air at 60 C. and trimethylsilylation carried out according to the method of Landerouin et al. (1987). Chromatography of the glucosinolate trimethylsilyl derivates was performed with a Hewlett Packard 5890 gas chromatograph (see FIG. 7). Glucosinolate content of seed meal (produced according to the method of Raney et al. 1987) was determined by gas chromatography using 0.1 gram of meal. For analysis of leaves or buds, the entire leaf or bud cluster was removed from the plant, immediately weighed and placed in a vial containing 2 ml of methanol, and a wash of the DEAE-Sephadex columns with 6% acetic acid was added between the 67% methanol and the water washes.

The moderately low glucosinolate *S. alba* population (Krzymanski et al. (1991) was grown in isolation. From this isolation, 975 individual plants were harvested and Tes-tape analyzed for total glucosinolate content. The 70 lowest glucosinolate plants were then analyzed by the above TMS analysis for a more comprehensive evaluation of their glucosinolate content. 8 plants were selected as having less than 0.2 µmoles/per g seed of p-hydroxybenzyl glucosinolate (FIG. 2, box 2). 15 progeny of these 8 plants were grown in the greenhouse and intercrossed. Open-pollinated (OP) seed was also produced on each plant and that was used for glucosinolate analysis (TMS analysis) to determine the genetic potential of those plants to produce or not produce seed glucosinolates. Twelve crosses out of the 192 made were selected for continuation (FIG. 2, box 3). Ten $F_1$ progeny of each of these were grown. Chain crossing was done between those which had different female parents in order to redistribute the genetic variation within the population. Open pollinated (OP) seed was also produced for glucosinolate analysis. Twenty-six crosses out of 318 made were selected as having <20 µmoles per g seed total aliphatic glucosinolate and <7.5 µmoles per g seed total indolyl glucosinolate and less than 0.1 µmoles per g seed p-hydroxybenzyl glucosinolate. Two $F_1$ progeny of each of these crosses were grown in isolation in the greenhouse and OP seed was produced (FIG. 2, box 4, for example, TO93-0860 ATCC No. PTA-2895).

$F_2$ progeny were grown in field isolation and 1,000 individual plants harvested. These were Tes-taped for low glucosinolate and 295 selected. Of the 295, 15 were selected by the TMS analysis as having the lowest glucosinolate content. These were composited and the progeny were then grown in the field and 1,000 individual plants harvested. The first 81 plants were composited and planted again in isolation. A total of 471 plants were harvested and analyzed for glucosinolate content (TMS analysis, internal standard; allyl glucosinolate). Of these, 2 plants were identified as having substantially zero benzyl glucosinolate and zero p-hydroxybenzyl glucosinolate content (FIG. 2, box 5; see Table 9).

TABLE 9

Glucosinolate content of
two individual plants selected from TO93-0860

| Plant/line | HOBut | Benzyl | HOBenzyl | Aliphatic | Indolyl | Total |
|---|---|---|---|---|---|---|
| TO93-0860 | 22.6 | 2.2 | 0.0 | 23.4 | 3.9 | 29.9 |
| 98RNSP082 | 17.1 | 0.0 | 0.0 | 17.6 | 11.6 | 30.9 |
| 98RNSP233 | 14.1 | 0.0 | 0.0 | 14.6 | 8.3 | 24.5 |

Example 3

Selection for Zero Erucic Acid *Sinapis alba*, Substantially Free of p-hydroxybenzyl Glucosinolate It has also been found that *S. alba* lines, according to the present invention, can be created that produce seed in which the oil is substantially free from erucic acid (<0.2% C22:1 by weight) and the remaining oil free meal is substantially free from p-hydroxybenzyl glucosinolate (<0.1 μmoles per 1 g of seed) but contains benzyl glucosinolate (FIG. 3; for example, TO 00-5647; ATCC No. PTA-2890).

A cross was made between a low p-hydroxybenzyl glucosinolate *S. alba* line 92-6669 (FIG. 2, 10 plants; containing benzyl glucosinolate) and a erucic acid (~1% erucic acid), high p-hydroxybenzyl glucosinolate *S. alba* line derived from BHL3-926 (FIG. 1; 6 plants). Based on the glucosinolate content of the ten 92-6669 parents, 8 crosses were selected for continuation.

Open pollinated $F_2$ seed was produced on six $F_1$ plants, which was planted in the field. One thousand individual plants were harvested. These were Tes-tape selected for low glucosinolate content, and 59 selected of which 23 were further selected on the basis of the TMS analysis (<0.1 μmole/g seed p-hydroxybenzyl glucosinolate). These 23 plants were used for half-seed selection for <1% erucic acid (selected 60 from 700 seeds analyzed). These moderately low erucic acid half-seeds were grown. Selfed and OP $F_4$ seed was produced. Sixteen of these 60 families were chosen for continuation on the basis of lowest p-hydroxybenzyl glucosinolate content and lowest erucic acid content. Thirty-six half-seeds of 314 analyzed were selected and crossed with a high oil content line (Olsson 1974) in an attempt to increase oil content in this germplasm.

It was recognized that the low (zero) erucic acid parent selected from BHL3-926 contained the minor allele for erucic acid (>0.5% to <1.5%) which prevents the re-selection of true breeding of low erucic acid (comprising <0.2%, preferably <0.1%, C22:1 by weight) individuals from the cross with the high oil content line. Therefore, the $F_1$ of this last cross (21 plants) was crossed with a true breeding, low erucic acid line (10 plants) that had been developed (FIG. 1; TO93-0930) to introduce genetic variability for low erucic acid into the cross. Sixty-three $F_1$ plants from the 21 crosses (3 from each) were grown. Selfed and OP $F_2$ seed was produced. The $F_2$ seed was analyzed for glucosinolate content (TMS analysis) and 20 plants with an intermediate level of p-hydroxybenzyl glucosinolate selected (<152 μmoles/g seed). Selfed seed of these plants were half-selfed (600 total) for high oleic acid content and <0.1% erucic acid. The 118 selected plants were then further selected for low p-hydroxybenzyl glucosinolate content by leaf analysis (TMS analysis). Twenty-two of the 118 plants analyzed had a low content and were clearly different from the rest by this population (expected 25% to be low if the prior selection of heterozgotes through selection of intermediate levels of seed p-hydroxybenzyl glucosinolate was successful.) These were crossed with the high oil content line (Olsson 1974, 6 plants). Forty high glucosinolate plants were also kept for comparison. Selfed and OP seed was also produced on all plants. Glucosinolate analysis of the OP $F_3$ seed of the 18 surviving low p-hydroxybenzyl glucosinolate plants revealed that 17 were indeed <0.1 μmoles/g p-hydroxybenzyl glucosinolate.

From the fatty acid analysis of the $F_3$ seed of these 17 plants, 15 crosses to the high oil content line were selected for continuation (high 18:1, low 18:3 and <0.2% erucic acid). Four plants of each the 15 selected crosses were grown and OP $F_2$ seed produced. A total of 4,896 $F_2$ seed was half-seed analyzed for fatty acid composition and 1.081 selected. Of the 1,007 surviving plants after transplanting 260 were selected as low p-hydroxybenzyl glucosinolate on the basis of leaf analysis (TMS analysis). OP $F_3$ seed was produced on these plants. A total of 181 plants were progeny evaluated in a single row (3 meter), two replicate nursery. The harvested seed of the rows was used for oil content determination. The reserve $F_3$ seed (12 seeds) of the 11 highest oil content lines was advanced further by half-seed selection for fatty acid composition and bud analysis for low p-hydroxybenzyl glucosinolate content. Seventy-one plants were grown and OP $F_4$ seed harvested. Thirty-three of these $F_3$ plants (three plants from each of the 11 $F_3$ lines were also crossed with the high oil content line from Svalöf (Olsson 1974, 12 plants). Nine plants were used in a cross with the low p-hydroxybenzyl glucosinolate, low benzyl glucosinolate line (see FIG. 5). Forty-three $F_4$ lines were progeny evaluated, and 38 (the highest oleic acid, low linolenic acid, low p-hydroxybenzyl glucosinolate, low C22:1) of these 43 lines were composited to form accession TO 00-5647 (FIG. 3; Tables 4 and 5).

Example 4

Figure 5:
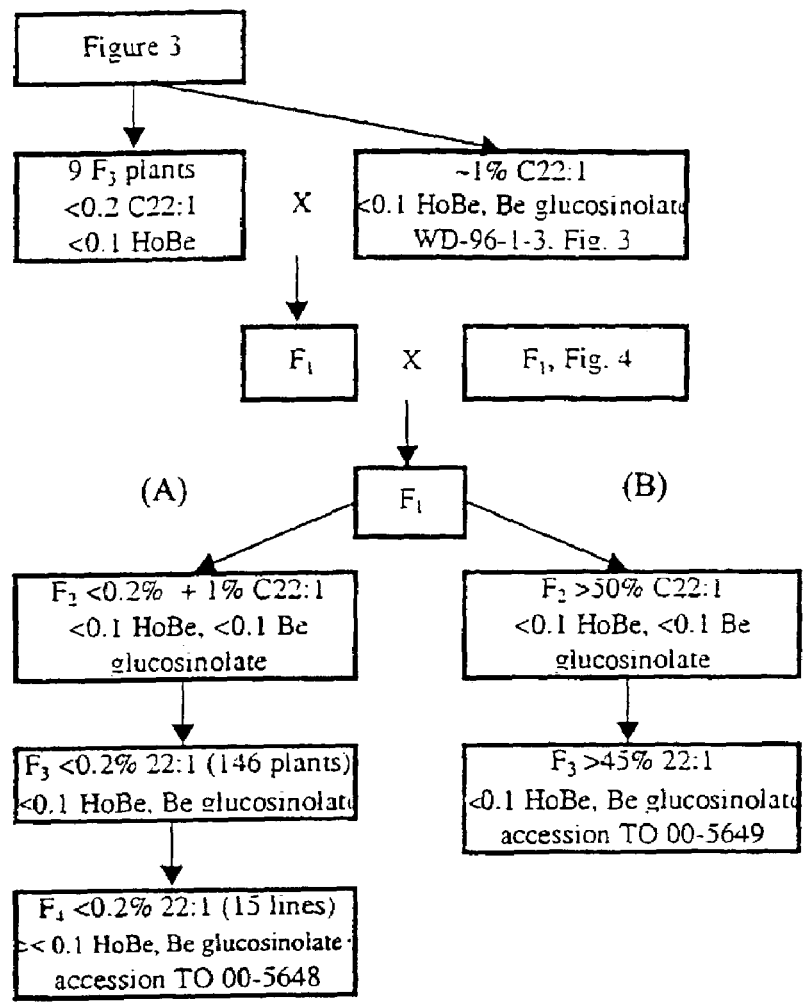
FIG. 5 outlines the development of a low erucic acid, low p-hydroxybenzyl glucosinolate and low benzyl glucosinolate *S. alba* (for example, but not limited to TO 00-5648; ATCC No. PTA 2891) in FIG. 5(A), and in FIG. 5(B), the development of a high erucic acid low p-hydroxybenzyl glucosinolate and low benzyl glucosinolate *S. alba*, for example, but not limited to TO 00-5649 (ATCC No. PTA 2892).

Selection for High Erucic Acid *Sinapis alba* Substantially Free of p-hydroxybenzyl Glucosinolate It has further been found that *S. alba* lines, according to the present invention, can be created that produce seed in which the seed oil contains very high concentrations of erucic acid (>45% C22:1 by weight) and the remaining meal is substantially free from p-hydroxybenzyl glucosinolate (FIG. 5; for example, accession TO 00-5650; ATCC No. PTA-2893).

This was achieved through a cross between the low p-hydroxybenzyl glucosinolate *S. alba* line 92-6669 (18 plants, FIG. 2) and the high erucic acid *S. alba* variety Sabre (10 plants, 51.4% C22:1 by weight, Table 5; developed by Agriculture and Agri-Food Canada, Saskatoon Research Centre; FIG. 4). Based on the TMS analysis of the 92-6669 parent line, 8 of the 18 crosses were selected for continuation. Six $F_1$ plants of each of these 8 crosses were grown and OP $F_2$ seed produced. This seed was sown in a field isolation and individual plants harvested. By Tes-tape 49 of 1,120 plants were selected as moderately low glucosinolate. Using TMS analysis 13 of these 49 were identified as comprising low p-hydroxybenzyl glucosinolate. The $F_3$ seed of these 13 plants was half-seed analyzed for high erucic acid content and half-seeds >54% selected.

Thirty-six 'high' erucic acid plants were grown and selfed and OP $F_4$ seed harvested. By TMS analysis of the OP seed, 10 lines were advanced. Twenty-two half-seed selected, high erucic acid plants from these lines were then crossed with the high oil content line (Olsson 1974). Nineteen $F_1$ plants from 14 crosses were grown and OP $F_2$ seed harvested. These were half-seed selected for high erucic acid content (>54%). Forty-three plants were selected and 39 survived to maturity to produce $F_3$ seed. Of 288 half-seed analyses done on the $F_3$ seed, 125 were selected having >56% erucic acid. By leaf TMS analysis, 36 low p-hydroxybenzyl glucosinolate plants were selected and crossed with the high oil content line (Olsson 1974). The harvested $F_4$ seed of all the low p-hydroxybenzyl glucosinolate parent lines was analyzed by TMS analysis and all were found to comprise low p-hydroxybenzyl glucosinolate. Based on the fatty acid analysis of these parent lines (parent >52% erucic acid), 12 crosses were advanced. Fifty-two $F_1$ plants were grown and OP $F_2$ seed harvested. Thirty-six seeds from each of the 52 lines were analyzed for fatty acid content and 9 were selected (>50% erucic acid) from each for a total of 460 half-seed $F_2$ plants grown. By leaf TMS analysis, 105 plants were selected (low p-hydroxybenzyl glucosinolate) and $F_3$ seed produced on 97 of these plants.

Based on the fatty acid analysis and TMS analysis done on the harvested $F_3$ seed, 16 $F_3$ lines were composited (for example, accession TO 00-5650, ATCC No. PTA-2893), which is substantially free from p-hydroxybenzyl glucosinolate (Table 6) and high in erucic acid (>50% C22:1, Table 5). Accession TO 00-5650 (ATCC No. PTA-2893) is suitable for the breeding of high erucic acid industrial oil *S. alba* which makes it possible to utilize the meal as a high protein animal feed because of it low glucosinolate content. Also based on this analysis, 22 $F_3$ lines were advanced by half-seed selection and leaf TMS analysis (selected 44 plants from these 22 lines, 12 seeds of each analyzed). These selected plants were crossed again to the high oil content line (Olsson 1974) and $F_1$ seed produced.

Example 5

Selection for (a) Zero Erucic Acid, Low p-hydroxybenzyl Glucosinolate, Low Benzyl Glucosinolate *Sinapis alba*; and (b) High Erucic Acid, Low p-hydroxybenzyl Glucosinolate, Low Benzyl Glucosinolate *Sinapis Alba*

It has also been found that *S. alba* lines, according to the present invention, can be created that in addition to comprising low p-hydroxybenzyl glucosinolate they comprise low benzyl glucosinolate (FIGS. 3 and 5, for example, WD-96-1-3). Low benzyl glucosinolate plants were isolated from the $F_3$ generation of the cross: 92-6669 (a low p-hydroxybenzyl glucosinolate line) and BHL3-926 (comprising ~1% erucic acid; FIG. 3) by half-seed selection and leaf TMS analysis.

To create low glucosinolate *S. alba* plants (low p-hydroxybenzyl and low benzyl glucosinolate) in combination with low erucic or high erucic acid contents, a cross was made between the 11 $F_3$ low erucic acid, and low p-hydroxybenzyl glucosinolate plants (described in FIG. 3, a subset of the plants that eventually were composited to make accession TO 00-5647, ATCC No. PTA-2890) and the ~1% erucic acid, low benzyl glucosinolate line WD-96-1-3 (1 plant, FIG. 5). Crossed $F_1$ seed was harvested from 9 of these plants. The $F_1$ generation of this cross (20 plants: 4 plants from each of 5 of the 9 crosses made) was then crossed with the $F_1$ (18 plants) of the cross: high erucic acid (>55% C22:1), low p-hydroxybenzyl glucosinolate (accession TO 00-5650) by high oil *S. alba* (Olsson 1974) (FIG. 4), to produce a segregating population that upon selection would yield:

a) low erucic acid, low p-hydroxybenzyl glucosinolate, low benzyl glucosinolate, high oil content *S. alba*; and b) high erucic acid, low p-hydroxybenzyl glucosinolate, low benzyl glucosinolate, high oil content *S. alba*.

A total of 252 $F_1$ plants (~12 plants from all 20 of the female parents) were grown and selfed $F_2$ seed harvested from 234 of them. A total of 350 zero (<0.2%) erucic acid $F_2$ seeds were half-seed selected from 2,800 seeds analyzed (~12 from each of the 234 $F_1$ plants), and by leaf TMS analysis 11 were selected (low p-hydroxybenzyl glucosinolate and low benzyl glucosinolate. OP $F_3$ seed was produced on these 11 plants. From analysis of 10 $F_3$ seeds of each plant it was determined that all plants were indeed low erucic acid and low p-hydroxybenzyl, low benzyl glucosinolate. The $F_3$ seed was then half-seed selected for high oleic acid, low linolenic content (996 seeds analyzed, 146 selected). From fatty acid and TMS analysis of the harvested $F_4$ seed from each of these plants, 15 plants were selected (Table 10) and composited (to make accession TO 00-5648; ATCC No. PTA-2891). This composite is zero (<0.2%) erucic acid, and zero (<0.1 μmoles per gm seed) p-hydroxybenzyl and benzyl glucosinolate (see Tables 5 and 6).

TABLE 10

Analysis for percent fatty acid content (%) and glucosinolate content (μmoles/g seed) on OP seed of selected low erucic acid $F_3$ plants.

| | Fatty acid content (%) | | | | | | | | | | Glucosinolate content(μmole/g seed) | | | | | |
|---|---|---|---|---|---|---|---|---|---|---|---|---|---|---|---|---|
| $F_3$ Plant | C16:0 | C16:1 | C18:0 | C18:1 | C18:2 | C18:3 | C20:0 | C20:1 | C22:0 | C22:1 | HoBu | Benz | HoBe | Aliphatic | Indolyl | Total G |
| 4731-1 | 3.5 | 0.3 | 1.2 | 74.8 | 7.6 | 8.9 | 0.4 | 1.4 | 0.2 | 0.1 | 13.2 | 0.0 | 0.5 | 13.3 | 8.7 | 22.8 |
| 4731-10 | 3.2 | 0.3 | 1.2 | 74.8 | 8.0 | 8.6 | 0.4 | 1.3 | 0.2 | 0.1 | 10.1 | 0.0 | 0.1 | 10.2 | 7.1 | 18.0 |
| 4731-12 | 3.5 | 0.3 | 1.2 | 70.3 | 9.6 | 11.3 | 0.4 | 1.2 | 0.2 | 0.1 | 5.6 | 0.0 | 0.0 | 5.7 | 4.3 | 10.4 |
| 4731-2 | 3.8 | 0.3 | 1.3 | 70.1 | 8.3 | 13.0 | 0.4 | 1.0 | 0.2 | 0.0 | 15.5 | 0.0 | 0.1 | 15.6 | 5.0 | 22.0 |
| 4731-4 | 3.6 | 0.3 | 1.4 | 71.3 | 7.9 | 12.1 | 0.4 | 1.1 | 0.2 | 0.0 | 16.4 | 0.0 | 0.3 | 16.5 | 6.2 | 24.0 |
| 4731-6 | 3.4 | 0.3 | 1.6 | 72.7 | 7.7 | 10.4 | 0.5 | 1.3 | 0.2 | 0.1 | 12.7 | 0.0 | 0.5 | 12.8 | 6.3 | 20.1 |
| 4734-5 | 3.5 | 0.3 | 1.6 | 72.1 | 7.1 | 10.8 | 0.5 | 1.7 | 0.2 | 0.4 | 13.4 | 0.0 | 0.0 | 13.6 | 8.1 | 22.4 |
| 4734-9 | 3.4 | 0.4 | 2.0 | 76.0 | 6.4 | 7.6 | 0.6 | 1.2 | 0.3 | 0.1 | 7.8 | 0.0 | 0.1 | 7.8 | 4.8 | 13.1 |
| 4735-18 | 3.8 | 0.3 | 1.8 | 70.3 | 8.2 | 11.6 | 0.6 | 1.2 | 0.2 | 0.1 | 13.6 | 0.0 | 0.0 | 13.8 | 6.9 | 21.3 |
| 4737-13 | 3.5 | 0.2 | 1.4 | 70.8 | 8.0 | 12.5 | 0.4 | 1.2 | 0.2 | 0.1 | 18.1 | 0.0 | 0.0 | 18.2 | 7.2 | 25.7 |
| 4738-1 | 3.5 | 0.3 | 1.4 | 71.0 | 8.3 | 12.1 | 0.4 | 1.1 | 0.2 | 0.0 | 8.9 | 0.0 | 0.0 | 9.0 | 5.0 | 14.5 |
| 4738-7 | 3.5 | 0.3 | 1.5 | 72.0 | 8.1 | 10.9 | 0.4 | 1.2 | 0.2 | 0.0 | 13.4 | 0.0 | 0.0 | 13.5 | 8.2 | 22.0 |
| 4738-8 | 3.3 | 0.3 | 1.7 | 73.1 | 7.0 | 11.2 | 0.5 | 1.2 | 0.2 | 0.0 | 9.7 | 0.0 | 0.0 | 9.9 | 7.4 | 17.9 |
| 4739-11 | 3.4 | 0.2 | 1.4 | 70.4 | 7.7 | 12.7 | 0.5 | 1.4 | 0.2 | 0.1 | 15.1 | 0.0 | 0.0 | 15.4 | 7.1 | 22.6 |
| 4739-9 | 3.8 | 0.4 | 1.4 | 70.6 | 8.6 | 11.1 | 0.6 | 1.4 | 0.2 | 0.1 | 15.7 | 0.0 | 0.0 | 16.4 | 7.7 | 24.7 |
| Average | 3.5 | 0.3 | 1.5 | 72.0 | 7.9 | 11.0 | 0.5 | 1.3 | 0.2 | 0.1 | 12.6 | 0.0 | 0.1 | 12.8 | 6.7 | 20.1 |

From 2,800 $F_2$ half-seeds analyzed, 246 high erucic acid (>50%) selections were also made (FIG. 5). By leaf TMS analysis, 15 low p-hydroxybenzyl and low benzyl glucosinolate plants were selected. OP F3 seed was produced on these. From fatty acid and TMS analysis of the harvested $F_3$ seed from each of these plants, 13 plants were selected (Table 11) and composited (to make accession TO 00-5649; ATCC No. PTA-2892). This composite is high (>45%) erucic acid, and low (<0.1 μmoles per g seed) p-hydroxybenzyl and benzyl glucosinolate (see Tables 5 and 6).

Selections in $F_2$ and $F_3$ generations yielded the desired types:
a) accession TO 00-5648; and
b) accession TO 00-5649.

The breeding approach outlined in Example 5 is unique in that it allows the breeding of the two types, edible oil and industrial oil to be developed from the same cross which has major advantages from the standpoint of optimizing the breeding work.

TABLE 11

Analysis for fatty acid content (%)
and glucosinolate content (μmoles/g seed) on OP seed of selected $F_2$ high erucic acid plants.

| $F_2$ Plant | Fatty acid content (%) | | | | | | | | | | Glucosinolate content(μmole/g | | | | |
|---|---|---|---|---|---|---|---|---|---|---|---|---|---|---|---|
| | C16:0 | C18:0 | C18:1 | C18:2 | C18:3 | C20:0 | C20:1 | C22:0 | C22:1 | HoBu | Benz | HoB | Aliphatic | Indolyl | Total G |
| 3824-2 | 2.20.3 | 0.9 | 18.8 | 6.8 | 10.1 | 0.6 | 8.5 | 0.7 | 44.5 | 22.8 | 0.0 | 0.1 | 23.0 | 15.7 | 39.6 |
| 3838-2 | 2.20.3 | 0.7 | 19.9 | 7.1 | 10.7 | 0.5 | 8.3 | 0.5 | 44.2 | 60.4 | 0.0 | 0.1 | 61.1 | 12.2 | 75.5 |
| 3838-5 | 2.00.2 | 0.7 | 21.9 | 7.3 | 9.2 | 0.5 | 7.9 | 0.5 | 44.2 | 41.4 | 0.0 | 0.1 | 41.7 | 8.4 | 51.2 |
| 3871-1 | 2.10.2 | 0.9 | 18.1 | 6.2 | 9.0 | 0.6 | 8.9 | 0.6 | 47.4 | 26.4 | 0.0 | 0.1 | 27.3 | 7.3 | 35.4 |
| 3871-2 | 2.30.3 | 0.7 | 17.1 | 6.2 | 10.8 | 0.5 | 7.8 | 0.5 | 47.9 | 45.6 | 0.0 | 0.1 | 47.0 | 10.4 | 58.4 |
| 3898-2 | 2.10.3 | 0.8 | 15.5 | 7.4 | 8.4 | 0.5 | 6.0 | 0.6 | 51.6 | 31.2 | 0.0 | 0.1 | 32.2 | 7.6 | 41.1 |
| 3902-1 | 2.80.3 | 0.7 | 17.4 | 7.0 | 9.6 | 0.6 | 8.2 | 0.6 | 47.4 | 18.7 | 0.0 | 0.0 | 19.2 | 3.8 | 24.0 |
| 4144-2 | 2.40.3 | 1.0 | 20.0 | 6.7 | 7.9 | 0.7 | 8.6 | 0.6 | 46.5 | 18.7 | 0.0 | 0.6 | 19.4 | 11.8 | 32.8 |
| 4146-1 | 2.30.2 | 0.8 | 19.4 | 8.5 | 7.6 | 0.5 | 7.1 | 0.6 | 46.7 | 29.1 | 0.0 | 0.0 | 30.3 | 9.5 | 40.5 |
| 4150-1 | 2.20.3 | 0.7 | 14.9 | 7.4 | 9.6 | 0.5 | 6.2 | 0.6 | 51.1 | 24.8 | 0.0 | 0.0 | 25.4 | 10.3 | 36.8 |
| 4150-2 | 2.60.3 | 0.7 | 15.2 | 8.6 | 10.3 | 0.4 | 7.4 | 0.5 | 47.6 | 29.5 | 0.0 | 0.0 | 30.0 | 7.6 | 39.0 |
| 4164-1 | 2.20.2 | 0.8 | 23.5 | 7.3 | 7.0 | 0.5 | 9.6 | 0.5 | 42.8 | 27.5 | 0.0 | 0.2 | 29.4 | 8.0 | 38.5 |
| 4176-2 | 1.80.2 | 0.8 | 19.1 | 8.2 | 9.1 | 0.5 | 7.5 | 0.6 | 46.1 | 33.3 | 0.0 | 0.1 | 35.6 | 10.2 | 46.7 |
| Average | 2.20.3 | 0.8 | 18.5 | 7.3 | 9.2 | 0.5 | 7.8 | 0.6 | 46.8 | 31.5 | 0.0 | 0.1 | 32.4 | 9.4 | 43.0 |

All citations are herein incorporated by reference.

The present invention has been described with regard to preferred embodiments. However, it will be obvious to persons skilled in the art that a number of variations and modifications can be made without departing from the scope of the invention as described herein.

REFERENCES

Bell, J. M., G. Rakow, and R. K. Downey 2000. Comparisons of amino acid and protein levels in oil-extracted seeds of Brassica and Sinapis species, with observations on environmental effects. Can. J. Anim. Sci. 80: 169-174.

Brandt, S. 1992. Depth, rates and dates of seeding and yield of yellow mustard (Sinapis alba L.) in west central Saskatchewan. Can. J. Plant Sci. 72:351-359.

Brown J., J. B. Davis, A. P. Brown, D. A. Erickson, and L. Seip 1999. Developing Canola-Quality cultivars of yellow mustard (Sinapis alba L.) Proc. 10$^{th}$ International Rapeseed Congress, Canberra, Australia, 6 pages.

Downey, R. K., and R G. Rakow 1995. Mustard. In: Harvest of Gold. The history of field crop breeding in Canada. Edited by A. E. Slinkard and D. R. Knott. University of Saskatchewan. University Extension Press.

Drost, W. J., G. Rakow and J. P. Raney 1999a. Inheritance of erucic acid content in yellow mustard (Sinapis alba L.). Proc. 10$^{th}$ International Rapeseed Congress, Canberra, Australia, 4 pages.

Drost, W. J., G. Rakow and J. P. Raney 1999b. Inheritance of glucosinolate content in yellow mustard (Sinapis alba L.). Proc. 10$^{th}$ International Rapeseed Congress, Canberra, Australia, 5 pages.

Eskin N. A. M., M. Vaisey-Genser, S. Durance-Todd and R. Przybylski 1989. Stability of low linolenic acid canola oil to frying temperatures. JAOCS vol 66: 10811984.

Katepa-Mupondwa, F., G. Rakow and J. P. Raney 1999a. Developing oilseed yellow mustard (Sinapis alba L.) in western Canada. Proc. 10$^{th}$ International Rapeseed Congress, Canberra, Australia, 6 pages.

Katepa-Mupondwa, F., G. Rakow and J. P. Raney 1999b. Meal quality characteristics of yellow mustard (Sinapis alba L.). Proc. 10$^{th}$ International Rapeseed Congress, Canberra, Australia, 6 pages.

Krzymanski, J., T. Pietka, I. Ratajska, B. Byczanska and K. Krotka 1991. Development of low glucosinolate white mustard (Sinapis alba syn. Brassica hirta). Proc. 8$^{th}$ International Rapeseed Congress, Saskatoon, Vol. 5:1545-1548.

Landerouin, A., Quinsac, A. and Ribaillier, D. (1987). Optimization of silylation reactions of desuphoglucosinolates before gas chromatography. World Crops: Production, Utilization, Description, 13, 26-37.

Lein, K. A. 1970. Quantitative Bestimmungsmethoden für Samenglucosinolate in Brassica-Arten und ihre Anwendung in der Züchtung von glucosinolatarmem Raps. Z. Pflanzenzüchtg. 63:137-154.

Olsson, G. 1974. Continuous selection for seed number per pod and oil content in white mustard. Hereditas 77:197-204.

Prevot, A., J. L. Perrin, G. Laclaverie, Ph. Auge, and J. L. Coustille 1990, A New variety of low-linolenic Rapeseed oil; Characteristics and room-odor tests. JAOCS vol 67:161-164.

Raney, J. P., G. Rakow and T. Olson 1999. Selection for high oleic acid in 'zero' erucic acid Sinapis alba. Proc. 10$^{th}$ International Rapeseed Congress, Canberra, Australia, 4 pages.

Ranev, J. P., G. Rakow and T. Olson 1995a. Development of low erucic, low glucosinolate *Sinapis alba*. Proc. 9$^{th}$ International Rapeseed Congress, Cambridge, U. K. Vol. 2:416-418.

Raney, J. P., G. Rakow and T. Olson 1995b. Development of high erucic, low glucosinolate *Sinapis alba*. Proc. 9$^{th}$ International Rapeseed Congress, Cambridge, UK, Vol. 2:452-454.

Raney, J. P., Love, H. K., Rakow, G. F. W. and Downey, R. K. (1987). An apparatus for rapid preparation of oil and oil-free meal from *Brassica* seed. Fett Wissenschaft Technologie, 89, 235-237.

Scartth, R., S. R. Rimmer and P. B. E. McVetty 1994. Apollo low linolenic acid summer rape, Can J. Plant Sci. 75: 203-204.

Thies, W. (1980) Analysis of glucosinolates via "on-column" desulfation. Proceedings of Symposium "Analytical Chemistry of Rapeseed and its Products" Winnipeg, pp 66-71.

White P. J and L. A. Miller 1988: Oxidative stabilities of low-lionolenate, high sterate and common soybean oils. J. Am. Oil Chem. Soc. 65: 1334-1338

What is claimed is:

1. A seed characterized by a deposit selected from deposit numbers ATCC No. PTA-2889, ATCC PTA-2890, and ATCC PTA-2891.

2. A seed characterized by deposit number ATCC No. PTA-2889.

3. A seed characterized by deposit number ATCC No. PTA-2890.

4. A seed characterized by deposit number ATCC No. PTA-2891.

* * * * *

UNITED STATES PATENT AND TRADEMARK OFFICE
CERTIFICATE OF CORRECTION

PATENT NO. : 7,279,618 B2  
APPLICATION NO. : 10/204142  
DATED : October 9, 2007  
INVENTOR(S) : John Philip Raney and Gerhard F. Rakow It is certified that error appears in the above-identified patent and that said Letters Patent is hereby corrected as shown below:

TITLE PAGE, ITEM (75) INVENTORS:  
DELETE "(SK)" AND REPLACE WITH --(CA)--.

Signed and Sealed this

Twenty-fifth Day of March, 2008

JON W. DUDAS  
*Director of the United States Patent and Trademark Office*

UNITED STATES PATENT AND TRADEMARK OFFICE
CERTIFICATE OF CORRECTION

| | | |
|---|---|---|
| PATENT NO. | : 7,279,618 B2 | Page 1 of 1 |
| APPLICATION NO. | : 10/204142 | |
| DATED | : October 9, 2007 | |
| INVENTOR(S) | : John Philip Raney and Gerhard F. Rakow | |

It is certified that error appears in the above-identified patent and that said Letters Patent is hereby corrected as shown below:

Title Pg, Item (73) Assignee: should read,

Her Majesty the Queen in Right of Canada as Represented by the Minister of Agriculture and Agri-Food Signed and Sealed this Twenty-eighth Day of July, 2009

JOHN DOLL
*Acting Director of the United States Patent and Trademark Office*